(12) United States Patent
Patel

(10) Patent No.: US 9,918,912 B2
(45) Date of Patent: Mar. 20, 2018

(54) STABLE THREE-PHASED EMULSIONS

(71) Applicant: Mary Kay Inc., Addison, TX (US)

(72) Inventor: Amit Patel, Euless, TX (US)

(73) Assignee: Mary Kay Inc., Addison, TX (US)

( * ) Notice: Subject to any disclaimer, the term of this patent is extended or adjusted under 35 U.S.C. 154(b) by 0 days.

(21) Appl. No.: 15/000,850

(22) Filed: Jan. 19, 2016

(65) Prior Publication Data

US 2016/0128916 A1 May 12, 2016

Related U.S. Application Data

(60) Division of application No. 14/194,255, filed on Feb. 28, 2014, now Pat. No. 9,271,903, which is a continuation of application No. 12/253,624, filed on Oct. 17, 2008, now Pat. No. 8,691,248.

(60) Provisional application No. 61/035,666, filed on Mar. 11, 2008.

(51) Int. Cl.

| A61K 8/06 | (2006.01) |
|---|---|
| A61K 8/73 | (2006.01) |
| A61K 8/891 | (2006.01) |
| A61K 8/58 | (2006.01) |
| A61K 8/895 | (2006.01) |
| A61K 9/00 | (2006.01) |
| A61K 47/36 | (2006.01) |
| A61K 47/24 | (2006.01) |
| A61Q 1/02 | (2006.01) |
| A61Q 1/12 | (2006.01) |

(Continued)

(52) U.S. Cl.

CPC ............ *A61K 8/064* (2013.01); *A61K 8/066* (2013.01); *A61K 8/585* (2013.01); *A61K 8/73* (2013.01); *A61K 8/891* (2013.01); *A61K 8/895* (2013.01); *A61K 9/0014* (2013.01); *A61K 47/24* (2013.01); *A61K 47/36* (2013.01); *A61Q 1/02* (2013.01); *A61Q 1/12* (2013.01); *A61Q 19/00* (2013.01); *A61Q 19/008* (2013.01); *B01F 17/0071* (2013.01); *A61K 2800/30* (2013.01); *A61K 2800/49* (2013.01); *A61K 2800/596* (2013.01)

(58) Field of Classification Search
None
See application file for complete search history.

(56) References Cited

U.S. PATENT DOCUMENTS

| 2,798,053 A | 7/1957 | Brown .......................... 521/38 |
| 3,755,560 A | 8/1973 | Dickert et al. ............. 514/772.6 |
| 4,421,769 A | 12/1983 | Dixon et al. .................. 514/772 |

(Continued)

FOREIGN PATENT DOCUMENTS

| EP | 0 345 075 | 12/1989 |
| EP | 0 612 759 | 10/1996 |

(Continued)

OTHER PUBLICATIONS

"Advances in the use of silicones in cosmetics," A&E Connock (Perfumery & Cosmetics) LTD, pp. 38-40, Jan./Feb. 1998.

(Continued)

*Primary Examiner* — Bethany P Barham
*Assistant Examiner* — Barbara S Frazier
(74) *Attorney, Agent, or Firm* — Norton Rose Fulbright US LLP

(57) ABSTRACT

Disclosed is a water-in-silicone emulsion comprising a discontinuous water phase, a continuous silicone phase, and a silicone polyglucoside containing emulsifier, wherein the discontinuous water phase does not include a salt.

20 Claims, 6 Drawing Sheets

(51) Int. Cl.
*A61Q 19/00* (2006.01)
*B01F 17/54* (2006.01)

(56) References Cited

U.S. PATENT DOCUMENTS

| | | | |
|---|---|---|---|
| 4,509,949 A | 4/1985 | Huang et al. | 8/558 |
| 5,011,681 A | 4/1991 | Ciotti et al. | 510/136 |
| 5,087,445 A | 2/1992 | Haffey et al. | 424/59 |
| 5,216,033 A | 6/1993 | Pereira et al. | 514/63 |
| 5,304,334 A | 4/1994 | Lahanas et al. | 516/23 |
| 5,428,142 A | 6/1995 | O'Lenick, Jr. | 536/1.11 |
| 5,831,080 A | 11/1998 | Sejpka et al. | 536/124 |
| 5,942,216 A | 8/1999 | Herb et al. | 424/70.28 |
| 5,948,855 A | 9/1999 | Lin et al. | 524/837 |
| 5,958,435 A | 9/1999 | Fructus | 424/401 |
| 6,033,651 A | 3/2000 | Dolak et al. | 424/65 |
| 6,110,473 A | 8/2000 | Fitzpatrick et al. | 424/401 |
| 6,165,479 A | 12/2000 | Wheeler | 424/400 |
| 6,171,600 B1 | 1/2001 | Dahms | 424/401 |
| 6,177,600 B1 | 1/2001 | Netzer | 585/323 |
| 6,183,730 B1 | 2/2001 | Guskey et al. | 424/65 |
| 6,221,927 B1 | 4/2001 | Lin et al. | 521/64 |
| 6,235,298 B1 | 5/2001 | Naser et al. | 424/401 |
| 6,290,943 B1 | 9/2001 | Naser et al. | 424/70.15 |
| 6,322,801 B1 | 11/2001 | Lorenzi et al. | 424/402 |
| 6,358,500 B1 | 3/2002 | Simon | 424/70.12 |
| 6,410,038 B1 | 6/2002 | Lin et al. | 424/402 |
| 6,428,799 B1 | 8/2002 | Cen et al. | 424/402 |
| 6,464,966 B1 | 10/2002 | Simon | 424/70.12 |
| 6,491,928 B1 | 12/2002 | Smith, III | 424/401 |
| 6,491,933 B2 | 12/2002 | Lorenzi et al. | 424/401 |
| 6,916,464 B2 | 7/2005 | Hansenne et al. | 424/59 |
| 6,919,071 B2 | 7/2005 | Choulot et al. | 424/59 |
| 7,115,535 B1 | 10/2006 | Smith, III et al. | 442/123 |
| 7,226,590 B2 | 6/2007 | Chilcott et al. | 424/93.44 |
| 7,229,632 B2 | 6/2007 | Amalric et al. | 424/401 |
| 7,285,570 B2 | 10/2007 | Robinson et al. | 514/423 |
| 2002/0022040 A1 | 2/2002 | Robinson et al. | 424/401 |
| 2002/0159963 A1 | 10/2002 | Simon | 424/70.12 |
| 2003/0082129 A1 | 5/2003 | Buckingham et al. | 424/70.12 |
| 2004/0192649 A1 | 9/2004 | Bissett et al. | 514/62 |
| 2004/0258639 A1 | 12/2004 | Lindemann et al. | 424/59 |
| 2005/0207967 A1 | 9/2005 | Yoshii | 423/461 |
| 2006/0057175 A1 | 3/2006 | Ciccognani et al. | 424/405 |
| 2007/0020220 A1 | 1/2007 | Osborne | 424/70.14 |
| 2007/0041917 A1 | 2/2007 | Thomas | 424/59 |

FOREIGN PATENT DOCUMENTS

| | | |
|---|---|---|
| WO | WO 95/31967 | 11/1995 |
| WO | WO 97/17938 | 5/1997 |
| WO | WO 98/34652 | 8/1998 |
| WO | WO 99/11237 | 3/1999 |
| WO | WO 02/100358 | 12/2002 |
| WO | WO 02/100958 | 12/2002 |
| WO | WO 04/030644 | 4/2004 |
| WO | WO 04/065463 | 8/2004 |
| WO | WO 06/110271 | 10/2006 |
| WO | WO 07/010478 | 1/2007 |
| WO | WO 07/029187 | 3/2007 |
| WO | WO 07/053424 | 5/2007 |
| WO | WO 07/077541 | 7/2007 |

OTHER PUBLICATIONS

"Beyond rheology modification: hydrophilically modified silicone elastomers provide new benefits," Journal of Cosmetic Science, 54:193-205, Mar./Apr. 2003.

HLB Values Chart, http://www.theherbarie.com/files/resource-center/formulating/Emulsifiers_HLB_Values.pdf, accessed Feb. 23, 2011.

International Cosmetic Ingredient Dictionary and Handbook, 11th Ed., 2006.

International Search Report and Written Opinion issued in Application No. PCT/US2009/036325, dated Jul. 1, 2009.

McCutcheon's, Detergents and Emulsifiers, North American Edition, 1986, (pp. vii-viii only).

Seppic, "Montanov 68: An emulsifier in harmony with nature", www.SEPPIC.com, published Feb. 2002.

STABLE THREE-PHASED EMULSIONS

CROSS REFERENCE TO RELATED APPLICATIONS

This application is a divisional of U.S. application Ser. No. 14/194,255, filed Feb. 28, 2014, which is a continuation of U.S. application Ser. No. 12/253,624, filed Oct. 17, 2008 (now issued as U.S. Pat. No. 8,691,248), which claims the benefit of U.S. Provisional Application No. 61/035,666, filed Mar. 11, 2008. The contents of the referenced applications are incorporated into the present specification by reference.

BACKGROUND OF THE INVENTION

A. Field of the Invention

The present invention relates generally to stable three-phase emulsions that include an external aqueous-gel phase and an internal water-in-oil phase. The emulsions can be used in cosmetic, food, and pharmaceutical applications.

B. Description of Related Art

Emulsions have been used in the cosmetics and pharmaceutical fields. The most prevalent type of emulsions used are two-phase oil-in-water and water-in-oil emulsions. The use of three-phase emulsions has increased in recent times.

However, three-phased emulsions have been shown to have stability problems. For instance, U.S. Pat. No. 6,464,966 explains a frequently encountered stability problem with water-in-oil-in water emulsions, where the internal droplets of water from the water-in-oil primary phase migrate through the oil phase and into the external aqueous phase. This type of migration can result in the coalescence of the internal droplets and release of the same into the aqueous external environment. Ultimately, this migration can lead to phase inversion which results in an unstable two-phase oil-in-water emulsion and a generally unusable product.

U.S. Pat. Nos. 6,464,966 and 6,358,500 attempt to solve the stability problem by introducing partially or completely crosslinked organopolysiloxane elastomers having a polyoxyethylenated or polyoxypropylenated chain into the oil phase of a water-in-oil-water triple emulsion. The use of such elastomers can lead to increased costs in preparing the three-phase emulsion and require large amounts of energy to function properly.

U.S. Pat. Nos. 6,290,943 and 6,235,298 disclose water-in-oil-in-water emulsions. These patents appear to suggest that the stability of their emulsions hinge on the use of an isotropic aqueous outer phase. These patents also explain that the use of surfactants having an HLB value of greater than 10 and the amount of such surfactants within the emulsion can contribute to the instability of multiple phase emulsions.

SUMMARY OF THE INVENTION

In one non-limiting aspect, the inventor has discovered a unique three phase emulsion that includes an inner water-in-oil primary phase and an outer aqueous-gel secondary phase. The emulsion has been shown to exhibit increased stability, an increased capacity to hold water, and can be made using standard mixing procedures and without the use of an external heating source. In certain embodiments, the emulsion can have aesthetically pleasing tactile properties (e.g., easy to spread or rub on skin, non-greasy feel, etc.). The three-phase emulsion is stable when stored at room temperature (e.g., approximately between 20° C. to 25° C.) for 1 week and 45° C. for 4 weeks. In other aspects, the three-phase emulsion is stable when stored at room temperature for 4 weeks or when stored at 45° C. for 4 weeks.

One embodiment of the present invention concerns a stable three-phase emulsion. The emulsion can include an aqueous-gel outer phase and a water-in-oil inner phase. In certain aspects, the emulsion can include 10, 20, 30, 40, 50, 60, 70, 80, 90, 95, 96, 97, 98, 99%, or more or less, of water based on the total weight of the emulsion.

One of the discoveries made by the inventor is that the three-phase emulsion can remain stable in embodiments where the aqueous-gel outer comprises 50% by weight of the total weight of the emulsion. In particular embodiments, the aqueous-gel outer phase comprises no more than 50, 40, 30, 20, 10, 7.5, 5%, or less, by weight of the total weight of the emulsion.

As for the aqueous-gel outer phase itself, it can include at least 10, 20, 30, 40, 50, 60, 70, 80, 95, 96, 97, 98, 99%, or more or less, by weight of water based on the total weight of the aqueous-gel outer phase. The aqueous-gel outer phase can also include a gelling agent. Non-limiting examples of gelling agents are disclosed throughout this specification (examples include polymer-based compounds). The gelling agent can be present in a variety of amounts. For instance, the gelling agent can be present in an amount of from 1, 2, 3, 4, 5, 6, 7, 8, 9, 10, 15, 20%, or more or less, by weight, based on the total weight of the aqueous-gel outer phase. In certain aspects, the aqueous-gel outer phase can have a viscosity ranging from 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, 100,000, 110,000, 120,000, 130,000, 140,000, 150,000, 160,000, 170,100, 180,000, 190,000, 200,000, 300,000, 400,000, 500,000 cps, or more or less, at 25° C. as measured on a Brookfield Viscometer using a TC spindle at 2.5 rpm. The aqueous-gel outer phase can also include an emulsifier. Non-limiting examples of emulsifiers include those having a hydrophilic-lipophilic balance (HLB) value of 10, 11, 12, 13, 14, 15, 16, 17, 18, or 19. Examples of such emulsifiers include taurate containing emulsifiers, sorbitol containing emulsifiers, sorbitan containing emulsifiers, and any combination thereof. The amount of the emulsifier in the aqueous-gel outer phase can vary. For instance, the amount of the emulsifier can range from 1, 2, 3, 4, 5, 6, 7, 9, 9, 10, 11, 12, 13, 14, 15%, or more or less, by weight based on the total weight of the aqueous-gel outer phase.

In other aspects, the water-in-oil inner phase of the emulsion can include at least 50, 60, 70, 80, 90, 95, 96, 97, 98, 99%, or more or less, by weight based on the total weight of the three-phase emulsion. As for the water-in-oil inner phase itself, it can include at least 10, 20, 30, 40, 50, 60, 70, 80, 90, 95, 96, 97, 98, 99%, or more or less, by weight of water based on the total weight of the water-in-oil inner phase. The water-in-oil inner phase can also include at least 5, 10, 20, 30, 40, 50, 60, 70%, or more or less, by weight of oil based on the total weight of the water-in-oil inner phase. In certain aspects, the water phase of the water-in-oil inner phase does not include a salt or a salt containing compound. In certain aspects, the aqueous gel-phase outer phase and/or the water phase of the water-in-oil inner phase can include salt sensitive ingredients. Salt sensitive means a compound or mixture which becomes unstable or changes its behavior in the presence of salt. Non-limiting examples of salt sensitive ingredients include sulfosuccinates, polyamides, stearimonium carbonates, carboxylic acids, ketones, and alcohols. The emulsions of the invention can also be prepared without using a stabilization agent.

The water-in-oil-inner phase can also include an emulsifier and or a co-emulsifier. Non-limiting examples of such emulsifiers are disclosed throughout this specification (e.g., salt-sensitive emulsifiers, heat sensitive emulsifiers, cationic emulsifiers, anionic emulsifiers, nonionic emulsifiers, zwitterionic emulsifiers, etc.). The emulsifier can be present in the inner phase from 1, 2, 3, 4, 5, 6, 7, 8, 9, 10, 11, 12, 13, 14, 15%, or more or less, by weight of the emulsifier based on the total weight of the water-in-oil inner phase. In certain aspects, the water-in-oil inner phase is dispersed within the aqueous-gel outer phase in individual droplets ranging from 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100 μm, or more or less, in size. In one embodiment, the emulsifier within the water-in-oil inner phase can be a silicone polyglucoside emulsifier. Such an emulsifier can include an octyl radical and/or a sugar glucoside bonded to individual Si—O monomers within the silicone backbone. In particular aspects, the sugar glucoside can be a 6 carbon monosaccharide ranging from 1-8 monomers. The monosaccharides can be bonded together via sugar ether linkages, and the glucoside can be bonded to the silicone backbone via an ethoxy bond. The molecular weight of the silicone polyglucoside emulsifier can be at least 450 daltons. In certain aspects, a co-emulsifier can be used within the water-in-oil inner phase. The co-emulsifier can be a glucolipid. The glucolipid can include an alkyl chain. The alkyl chain can vary from 8-20 carbons. The glucose portion of the glucolipid can be a 5 carbon monosaccharide. The alkyl chain can be bonded to the 5 carbon monosaccharide via a sugar ether linkage. The molecular weight of the glucolipid co-emulsifier can be at least 450 daltons. When the silicone polyglucoside emulsifier and glucolipid co-emulsifier are used together, the ratio of the silicone polyglucoside emulsifier to the glucolipid emulsifier can be between about 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, to about 25:1 by total weight of the water-in-oil-inner phase. Non-limiting examples of silicone polyglucoside emulsifiers and co-emulsifiers that can be used in the context of the present invention are described in European Patent 612,759 and U.S. Pat. No. 5,831,080, the contents of which are incorporated by reference.

The emulsifiers can include an alkyl dimethicone ethoxy siliconyl glucoside(polysaccharide) compound. In certain aspects, the water-in-oil inner phase can have a viscosity ranging from 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, 100,000, 110,000, 120,000, 130,000, 140,000, 150,000, 160,000, 170,100, 180,000, 190,000, 200,000, 300,000, 400,000, 500,000 cps, or more or less, at 25° C. as measured on a Brookfield Viscometer using a TC spindle at 2.5 rpm. The oil of the water-in-oil inner phase can be a silicone oil. In certain aspects, the silicone oil can be selected from the group consisting of cyclomethicones, aryl silicones, dimethicone copolyols, cyclopentasiloxanes, dimethicones, low molecular weight alkanes, low molecular weight esters, short chain siloxanes, and silicone acrylates.

In particular embodiments, the viscosity of the three-phase emulsion can range depending on the type of product or desired tactile properties of such a product. Non-limiting examples of the viscosity range of the three-phase emulsion include 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, 100,000, 110,000, 120,000, 130,000, 140,000, 150,000, 160,000, 170,100, 180,000, 190,000, 200,000, 300,000, 400,000, 500,000 cps, or more or less, at 25° C. as measured on a Brookfield Viscometer using a TC spindle at 2.5 rpm.

The three-phase emulsion can be used as a carrier to deliver active ingredients to a target site (such as skin). The active ingredient can be contained within the aqueous-gel outer phase, the oil phase of the water-in-oil inner phase, the water phase of the water-in-oil inner phase, or a combination of these phases. Multiple active ingredients can be loaded into the three-phase emulsion. In certain aspects, the emulsions can be formulated to release the actives in a time-dependent manner.

In particular aspects, the three-phase emulsion can consist of or consist essentially of an aqueous-gel outer phase and a water-in-oil emulsion inner phase.

A particular non-limiting three-phase emulsion of the present invention can include, consist of, or consist essentially of the following: (a) an aqueous-gel outer phase comprising no more than 10% to 50% by weight of the total weight of the emulsion, wherein the aqueous outer phase comprises: (i) 70% to 95% by weight of water based on the total weight of the aqueous-gel outer phase; (ii) a gelling agent present in an amount of from 5% to 10% by weight of the total weight of the aqueous-gel outer phase; (iii) a viscosity of 50,000 to 120,000 cps at 25° C. as measured on a Brookfield Viscometer using a TC spindle at 2.5 rpm; and contain (iv) an emulsifier having a hydrophilic-lipophilic balance (HLB) value of 10 to 19 present in an amount of from 2% to 5% by weight based on the total weight of the aqueous-gel outer phase; and (b) a water-in-oil inner phase comprising 50% to 95% by weight of the total weight of the emulsion, wherein the water-in-oil inner phase comprises: (i) 40% to 60% by weight of water based on the total weight of the water-in-oil inner phase; (ii) 20% to 50% by weight of oil based on the total weight of the water-in-oil inner phase; (iii) 3% to 8% by weight of an emulsifier or an emulsifier and co-emulsifier based on the total weight of the emulsion, wherein the emulsifier is a silicone polyglucoside emulsifier and the co-emulsifier is a glucolipid, wherein the ratio of the emulsifier to the co-emulsifier is between 5:1 to 25:1 based on the total weight of the water-in-oil inner phase; and (iv) a viscosity of 20,000 to 30,000 cps at 25° C. as measured on a Brookfield Viscometer using a TC spindle at 2.5 rpm; wherein the three-phase emulsion is stable. In certain aspects, such a three-phase emulsion can include a cosmetic or pharmaceutically active ingredient. The water phase of the water-in-oil inner phase does not include a salt in certain embodiments. The water phase can include salt sensitive ingredients. In particular aspects, the three-phase emulsion does not include a stabilization agent.

Also disclosed are topical skin care compositions, hair care compositions, pharmaceutical compositions (including oral, aerosol, liquid, injectible, topical), and food compositions that include emulsions of the present invention.

In another embodiment, there is disclosed a method of treating skin conditions comprising topical application of a composition comprising a three-phase emulsion of the present invention, where topical application of the composition treats the skin. Non-limiting examples of skin conditions that can be treated in the context of the present invention include pruritus, spider veins, lentigo, age spots, senile purpura, keratosis, melasma, blotches, fine lines or wrinkles, nodules, sun damaged skin, dermatitis (including, but not limited to seborrheic dermatitis, nummular dermatitis, contact dermatitis, atopic dermatitis, exfoliative dermatitis, perioral dermatitis, and stasis dermatitis), psoriasis, folliculitis, rosacea, acne, impetigo, erysipelas, erythrasma, eczema, and other inflammatory skin conditions. In certain non-limiting aspects, the skin condition can be caused by exposure to UV light, age, irradiation, chronic sun exposure, environmental pollutants, air pollution, wind, cold, heat, chemicals, disease pathologies, smoking, or lack of nutrition. The skin can be facial skin or non-facial skin (e.g., arms, legs, hands, chest, back, feet, etc.).

Also disclosed is a method of delivering a cosmetic or pharmaceutical active ingredient to skin comprising topically applying a composition comprising a cosmetic or pharmaceutical active ingredient and a three-phase emulsion of the present invention, wherein topical application of the composition delivers the cosmetic or pharmaceutical active ingredient to the skin.

In yet another embodiment there is disclosed a method of preparing a stable three phase emulsion of the present invention. The method can include mixing the aqueous-gel outer phase with the water-in-oil inner phase. In certain aspects, the method only include mixing the aqueous-gel outer phase with the water-in-oil inner phase. In even other embodiments, an external heat source is not used to prepare the emulsion or to mix the outer phase with the inner phase. The preparation process can be performed at room temperature (e.g., approximately between 20° C. to 25° C.). Mixing can be performed by any standard mixing procedure or apparatus. Non-limiting examples of mixing include slow impeller mixing, sweep mixing, high shear mixing, or any combination thereof. Slow impeller mixing can include using a 3 blade propeller connected to a Lab scale Caframo Mixer with a rotation speed of 500-1000 rpm. Sweep mixing can include using a Z-Bar blade with a rotation speed of <60 rpm for >10 minutes creating a slow turnover of the batch volume. High Shear mixing can include using a rotation speed of 1000-3000 rpm with a Greerco Lab scale homogenizer based on 1 kg of bulk per minute creating a high turnover of batch volume.

The mixing can be performed at room temperature. The mixing time can range. For instance the mixing can be performed for approximately 1, 2, 3, 4, 5, 6, 7, 8, 9, 10, 15, 20, 30, 40, 50, 60 minutes, 1, 2, 3, 4, 5, 6, 7, hours or more. For high shear mixing with a propeller, the propeller speed can range from approximately 1000, 1,500, 2,000, 2,500, 3,000, 3,500, 4,000 rpm, or more or less, per one kg of the bulk ingredients. In certain aspects, the mixing can include sweeping or slow impeller mixing followed by high shear mixing, or high shear mixing followed by sweeping or slow impeller. The method can include adding the aqueous-gel outer phase to the water-in-oil inner phase prior to and/or during mixing. The method can include adding the water-in-oil inner phase to the aqueous-gel outer phase prior to and/or during mixing. In certain aspects, the water-in-oil phase is prepared before the aqueous-gel outer phase. In other aspects, the aqueous-gel outer phase is prepared before the water-in-oil inner phase.

In a particular embodiment, there is disclosed a method of preparing the three-phase emulsion of the present invention which includes: (a) obtaining an aqueous-gel outer phase; (b) obtaining a water-in-oil inner phase; and (c) mixing the aqueous-gel outer phase with the water-in-oil inner phase at room temperature via sweeping or slow impeller mixing for approximately one to ten minutes followed by high-shear mixing for approximately 1 to 10 minutes to obtain a mixture, wherein the mixture is a stable three-phase emulsion. As noted above, an external heat source is not required to make the emulsion. Also, the aqueous-gel outer phase can be added to the water-in-oil inner phase prior to or during mixing or the water-in-oil inner phase can be added to the aqueous-gel phase prior to or during mixing.

Another aspect of the present invention includes a stable water-in-oil emulsion. This two phase emulsion (e.g., oil is the continuous phase whereas water is the discontinuous phase) can include (a) a water phase comprising 5, 10, 20, 30, 40, 50, 60, 70, 80, 90, 95% or more or less or any range therein by weight of water based on the total weight of the emulsion, wherein the water phase does not include a salt; (b) an oil phase comprising 5, 10, 20, 30, 40, 50, 60, 70, 80, 90, 95% or more or less or any range therein by weight of oil based on the total weight of the emulsion; (c) 1, 2, 3, 4, 5, 6, 7, 8, 10, 11, 2, 13, 14, 15% or more or less or any range therein by weight of an emulsifier or an emulsifier and co-emulsifier based on the total weight of the emulsion, wherein the emulsifier is a silicone polyglucoside emulsifier and the co-emulsifier is a glucolipid, wherein the ratio of the emulsifier to the co-emulsifier is between 5:1 to 25:1 based on the total weight of the emulsion; and (d) a viscosity of 20,000 to 30,000 cps at 25° C. as measured on a Brookfield Viscometer using a TC spindle at 2.5 rpm, wherein the water-in-oil emulsion is stable. The water-in-oil emulsion does not include a stabilization agent in certain embodiments. The water phase of this emulsion can include salt sensitive ingredients. In particular aspects, the emulsion does not include a stabilization agent. A unique aspect of the water-in-oil emulsion is that it can be used in a variety of embodiments. For instance it can be used in topical skin care compositions, hair care composition, pharmaceutical compositions, food compositions, etc. It can be used in compositions for treating skin conditions (including those disclosed above and throughout this specification), wherein the method of treating skin can include topical application of the water-in-oil emulsion (or a composition or product that includes the emulsion) to skin, wherein topical application treats skin. It can also be used to deliver cosmetic and/or pharmaceutical active ingredients to skin, where such a method can include topically applying the water-in-oil emulsion (or a composition or product that includes the emulsion) to skin, wherein topical application delivers the cosmetic or pharmaceutical active ingredient to the skin. In particular aspects, the water-in-oil emulsion can be used as an inner phase of a three-phase emulsion. The outer phase of such a three-phase emulsion can be an aqueous-gel outer phase. The aqueous-gel outer phase can include no more than 10% to 50% by weight of the total weight of the three-phase emulsion. The aqueous-gel outer phase can include: (a) 70% to 95% by weight of water based on the total weight of the aqueous-gel continuous phase; (b) a gelling agent present in an amount of from 5% to 10% by weight of the total weight of the aqueous-gel continuous phase; (c) a viscosity of 50,000 to 120,000 cps at 25° C. as measured on a Brookfield Viscometer using a TC spindle at 2.5 rpm; and/or (d) an emulsifier having a hydrophilic-lipophilic balance (HLB) value of 10 to 19 present in an amount of from 2% to 5% by weight based on the total weight of the aqueous-gel continuous phase.

Also disclosed is a method of preparing the water-in-oil two phase emulsion. Such a method can include mixing the water phase with the oil phase. An external heat source is not required to prepare the emulsion or to mix the outer phase with the inner phase. The preparation process can be performed at room temperature (e.g., approximately between 20° C. to 25° C.). Mixing can be performed by any standard mixing procedure or apparatus. Mixing can include sweeping or slow impeller mixing or high sheer mixing, or any combination thereof. The mixing can be performed at room temperature. The length of the total mixing process or of each mixing step can vary as needed (e.g., 1, 2, 3, 4, 5, 6, 7, 8, 9, 0, 15, 20, 25, 30, 35, 40, 45, 50, 55, 60, minutes, 1, 2, 3, 4, 5, 6, 7, or more hours). In certain embodiments, high sheer mixing can include propeller mixing at approximately 1500 to 3000 rpm per one kg of the bulk ingredients. The mixing step can include sweeping or slow impeller mixing followed by high shear mixing or high shear mixing followed by sweeping or slow impeller.

It is contemplated that any embodiment discussed in this specification can be implemented with respect to any compound, method, or composition of the invention, and vice versa.

In one embodiment, topical skin compositions that include the three-phase emulsion of the current invention are pharmaceutically or cosmetically elegant. "Pharmaceutically elegant" and/or "cosmetically elegant" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

"Topical application" means to apply or spread a composition onto the surface of keratinous tissue. "Topical skin composition" includes compositions suitable for topical application on keratinous tissue. Such compositions are typically dermatologically-acceptable in that they do not have undue toxicity, incompatibility, instability, allergic response, and the like, when applied to skin. Topical skin care compositions of the present invention can have a selected viscosity to avoid significant dripping or pooling after application to skin.

"Keratinous tissue" includes keratin-containing layers disposed as the outermost protective covering of mammals and includes, but is not limited to, skin, hair and nails.

The terms "about" or "approximately" are defined as being close to as understood by one of ordinary skill in the art, and in one non-limiting embodiment the terms are defined to be within 10%, within 5%, within 1%, or within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting," "reducing," or "prevention," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the invention. The invention may be better understood by reference to one or more of these drawings in combination with the detailed description of example embodiments presented here. The drawings are examples only and do not limit the claims.

DESCRIPTION OF ILLUSTRATIVE EMBODIMENTS

Figure 1:
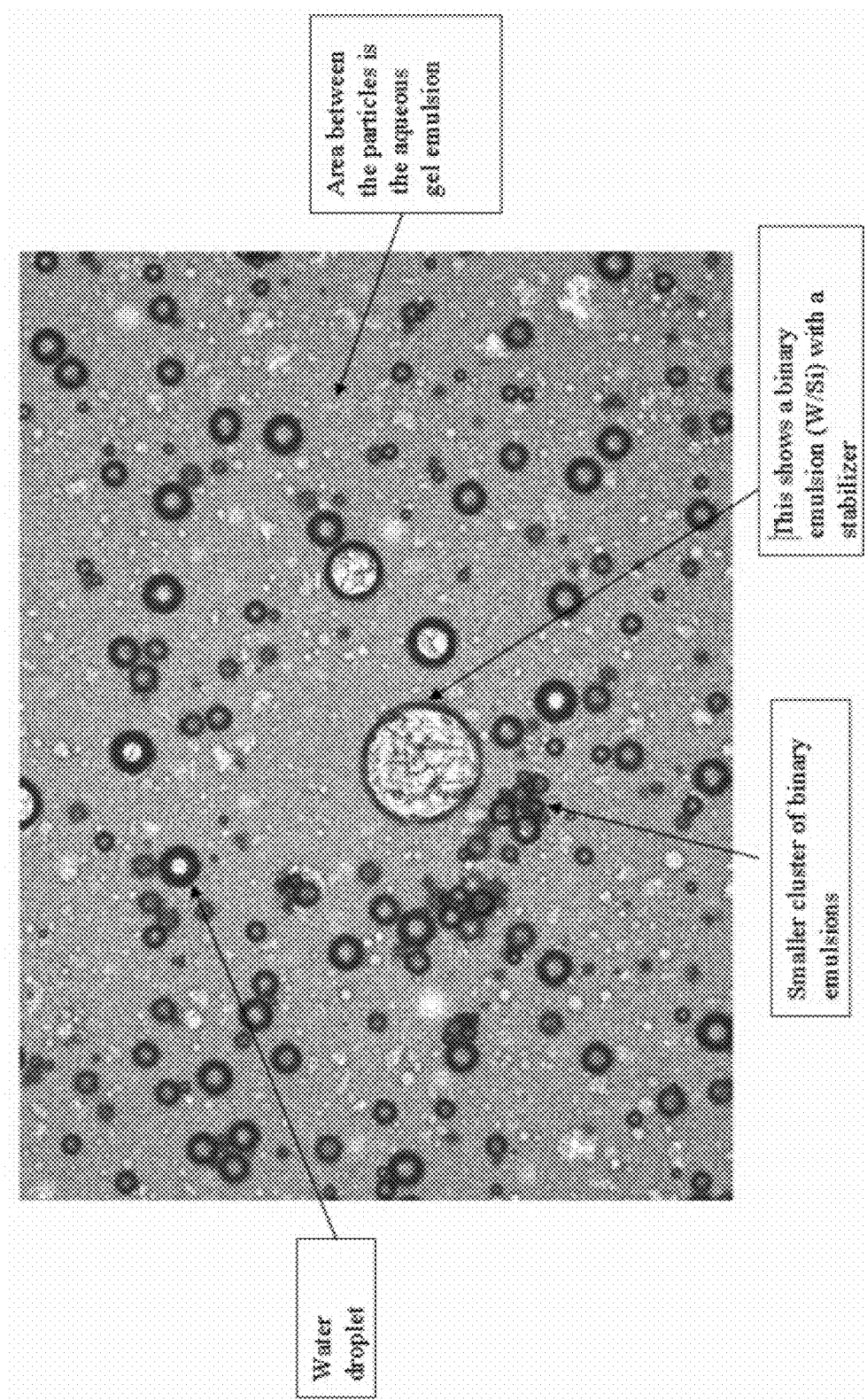
FIG. 1 is a micrograph of a three-phase emulsion of the present invention. The water-in-oil phase (referred to as "primary phase") includes 92.5% by weight of the total weight of the emulsion. The aqueous-gel outer phase (referred to as "secondary phase") includes 7.5% by weight of the total weight of the emulsion.

The inventor has discovered a unique combination of an aqueous-gel outer phase and a water-in-oil inner phase that allows for the creation of a stable three phase emulsion (e.g., water-in-oil emulsion in an aqueous-gel outer phase). This three-phase emulsion can include aesthetically pleasing tactile properties (e.g., easy to spread, non-greasy feel, etc.) and is capable of holding high amounts of water (e.g., a non-limiting amount includes 70% to 95% of water based on the total weight of the emulsion). The water holding capabilities of the three-phase emulsion have several benefits. For instance, increasing the amount of water delivered to skin allows for increased hydration of skin, which can increase the softness and suppleness of skin while also decreasing the appearance of dry or flaking skin. In addition, water is a relatively inexpensive ingredient in cosmetic, pharmaceutical, and food formulations. Therefore, the present three phase emulsion allows for the creation of a viable product while decreasing the costs of preparing such a product. Further, a wide variety of products can be obtained by adjusting the portions of the water-in-oil inner phase and aqueous-gel outer phases.

Another unique aspect of the three-phase emulsion is that it can be made by using standard mixing procedures and without the use of an external heating source. This can reduce the costs associated with preparing the emulsion and decrease the time it takes to make such an emulsion, while also increasing the stability of the emulsion (e.g., by not using heat to agitate the phases).

A more detailed and non-limiting description of the three-phase emulsion and how it can be made is provided in the following sections.

A. Aqueous-Gel Outer Phase

In certain embodiments, the aqueous-gel outer phase makes up between about 10% to about 50% by weight of the total weight of the emulsion. However, this range can be modified as desired (e.g., the aqueous-gel outer phase can comprise 1, 2, 3, 4, 5, 6, 7, 8, 9, 10, 15, 20, 25, 30, 35, 40, 45, 50, 55, 60, 65, 70, 75, 80, 85, 90, 95, 99%, or more or any integer therein of the total weight of the emulsion).

The aqueous phase can also include a gelling agent. Gelling agents include substances that can increase the viscosity of the aqueous-gel phase. Non-limiting examples include those known in the art (e.g., U.S. Pat. Nos. 5,087,445; 4,509,949; 2,798,053; International Cosmetic Ingredient Dictionary, 11$^{th}$ Ed., 2006). Specific examples include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

The viscosity of the aqueous-gel phase can be modified to a desired range by increasing or decreasing the amount of the gelling agent within this phase. There are many available methods that can be used to determine the viscosity of any given composition, including phases of an emulsion. For instance, viscosity of the three-phase emulsion, any phase within this emulsion, or any composition that includes the emulsion can be determined by using a T spindle at 2.5 rpm at room temperature (e.g., approximately 25° C.). A Brookfield Viscometer/Rheometer can be used. In certain aspects, the viscosity of the aqueous-gel outer phase is between 50,000 to 150,000 cps at 25° C. as measured on a Brookfield Viscometer using a TC spindle at 2.5 rpm. However, as explained elsewhere in this specification, the viscosity range can vary inside or outside this range, as desired.

Emulsifiers can be included in the aqueous-gel outer phase. The hydrophobic/lipophilic balance ("HLB value") (i.e., the balance between the hydrophilic and lipophilic portions of the molecule) can be modified as desired. Larger HLB value emulsifiers can result in a molecule that can be more soluble in water and can be used as an oil-in-water emulsifier. Smaller HLB value molecules can result in a molecule that can be more soluble in oil and can be used as a water-in-oil emulsifier. In certain aspects, the HLB value of the emulsifiers in the can be from about 10 to about 19 (including 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 16.0, 16.1, 16.2, 16.3, 16.4, 16.5, 16.6, 16.7, 16.8, 16.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0). In other aspects, the HLB value can extend outside this range, as needed). Non-limiting examples of such emulsifiers include taurate, sorbitol, or sorbitan containing emulsifiers (see, e.g., International Cosmetic Ingredient Dictionary, 11$^{th}$ Ed., 2006). Also contemplated are combinations of different taurate containing emulsifiers, combinations of different sorbitol containing emulsifiers, combination of different sorbitan containing emulsifiers, or combinations of taurate, sorbitol, and sorbitan containing emulsifiers. Non-limiting examples of sorbitol and sorbitan containing emulsifiers include Disodium Hydroxydecyl Sorbitol Citrate, Glyceryl/Sorbitol Oleate/Hydroxystearate, Hydroxyethyl Sorbitol, PEG-3/PPG-2 Glyceryl/Sorbitol Hydroxystearate/Isostearate, Polyoxypropylene Sorbitol Ricinoleate, PPG-8 Sorbitol Castor Oil, Rapeseed Oil Sorbitol Esters, Sunflower Seed Oil Sorbitol Esters, Anhydrosorbitol Trioleate, Anhydrosorbitol Tristearate, Dibenzalsorbitol, Lauric Acid, Sorbitol Monoester, PEG-20 Sorbitol Pentaisostearate, PEG-30 Sorbitol Pentaisostearate, PEG-40 Sorbitol Pentaisostearate, PEG-50 Sorbitol Pentaisostearate, Diglyceryl Sorbitan Tetraoctanoate, Fatty Acids, Olive, Monoesters with Sorbitan, Oleic Acid, Diester with Sorbitan, PEG-2 Sorbitan Beeswax, PEG-6 Sorbitan Beeswax, PEG-8 Sorbitan Beeswax, PEG-20 Sorbitan Beeswax, Polyethylene Glycol (100) Sorbitan Beeswax, Polyethylene Glycol 300 Sorbitan Beeswax, and Polyethylene Glycol 400 Sorbitan Beeswax. Non limiting examples of taurate containing emulsifiers include Acrylamide/Sodium Acryloyldimethyltaurate/Acrylic Acid Copolymer, Acrylamide/Sodium Acryloyldimethyltaurate Copolymer, Ammonium Acryloyldimethyltaurate/Beheneth-25 Methacrylate Crosspolymer, Ammonium Acryloyldimethyltaurate/Laureth-7 Methacrylate Copolymer, Ammonium Acryloyldimethyltaurate/Steareth-8 Methacrylate Copolymer, Ammonium Acryloyldimethyltaurate/Steareth-25 Methacrylate Crosspolymer, Ammonium Acryloyldimethyltaurate/Vinyl Formamide Copolymer, Ammonium Acryloyldimethyltaurate/VP Copolymer, Ammonium Polyacryloyldimethyl Taurate, Calcium Lauroyl Taurate, Dimethylacrylamide/Sodium Acryloyldimethyltaurate Crosspolymer, Hydroxyethyl Acrylate/Sodium Acryloyldimethyl Taurate Copolymer, and Potassium Methyl Cocoyl Taurate.

The aqueous-gel outer phase can include other ingredients known to those of ordinary skill in the art (see, e.g., International Cosmetic Ingredient Dictionary, 11$^{th}$ Ed., 2006), and those identified throughout this specification. Non-limiting examples of such ingredients include water, polyols, hydrophilic cosmecutical and/or pharmaceutical ingredients, etc., and mixtures thereof. The concentration ranges of these ingredients can vary as explained in other sections of this specification.

The aqueous-gel outer phase can be prepared by using techniques that are known in the art (see, e.g., Mitxhell and Schlossman, *The Chemistry and Manufacture of Cosmetics: Volume II—Formulating,* 2000; *Volume II Formulating*, Chapter 7, pages 135-150). For instance, this outer phase can be made by combining water, the selected gels or gelling agents, and preservative into a main vessel. The ingredients are subsequently homogenized by using standard mixing procedures, which results in the formulation of the aqueous-gel outer-phase.

B. Water-in-Oil Inner Phase

The inventor has discovered a water-in-oil emulsion that can be used alone, or in combination with a three-phase emulsion as a water-in-oil inner phase. The water-in-oil emulsion is an emulsion where the water phase is dispersed within the oil phase. In certain embodiments, the water-in-oil phase can make up 50% to 90% by weight of the total weight of the three-phase emulsion. However, this range can be modified as desired (e.g., the water-in-oil inner phase can comprise 1, 2, 3, 4, 5, 6, 7, 8, 9, 10, 15, 20, 25, 30, 35, 40, 45, 50, 55, 60, 65, 70, 75, 80, 85, 90, 95, 99%, or more or any integer therein of the total weight of the emulsion). A unique aspect of the water-in-oil emulsion is that the water phase does not require the use of a salt. Such an emulsion can also include salt sensitive ingredients. Further, the water-in-oil emulsion and the three-phase emulsion do not require the use of a stabilization agent.

The water phase can include ingredients that are known to those of ordinary skill in the art (see, e.g., International Cosmetic Ingredient Dictionary, 11$^{th}$ Ed 2006) and those that are disclosed throughout the specification. Non-limiting examples of such ingredients include water, polyols, hydrophilic cosmecutical and/or pharmaceutical ingredients, etc., and mixtures thereof. The concentration ranges of these ingredients can vary as explained in other sections of this specification.

The oil phase can also include ingredients that are known to those of ordinary skill in the art (see, e.g., International Cosmetic Ingredient Dictionary, 11$^{th}$ Ed., 2006) and those that are disclosed throughout the specification. Non-limiting examples of such ingredients include oils, fatty acids, fatty alcohols, waxes of natural or synthetic origin, hydrocarbon solvents, film formers, silicones, silicone polymers, fluorinated solvents, etc. The concentration ranges of these ingredients can vary as explained in other sections of this specification. Non-limiting examples of oils that can be used in the context of the present invention include: oils of plant origin (e.g., sweet almond oil, coconut oil, castor oil, jojoba oil, olive oil, rapeseed oil, groundnut oil, sunflower oil, wheat germ oil, maize germ oil, soy based oil, cotton oil, lucerne oil, poppy oil, marrow oil, evening primrose oil, millet oil, barley oil, rye oil, safflower oil, canelle nut tree oil, passionflower oil, hazelnut oil, palm oil, shea butter, apricot stone oil, Alexandria laurel tree oil, sysymbrium oil, avocado oil, calendula oil, etc.); modified plant oils (e.g., products known under INCI designations Apricot Kernel Oil PEG-6 esters, Olive Oil PEG-6 esters, etc.); oils of natural origin (e.g., perhydrosqualene, squalene, etc.); mineral oils (e.g., liquid paraffin, mineral oils originating from petroleum fractions such as isoparaffins having a boiling point between 300 and 400° C., etc.); synthetic oils (e.g., fatty acid esters such as butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate, propylene glycol dicaprylate, ester derivatives of lanolic acid, such as isopropyl lanolate, isocetyl lanolate, monoglycerides, triglycerides such as glycerol triheptanoate, alkylbenzoates, isoparaffins, polyalphaolefins, polyolefins, such as polyisobutylene, synthetic isoalkanes such as isohexadecane, isododecane, perfluorinated oils, silicone oils, etc.). Non limiting examples of silicone oils include dimethyl polysiloxanes, methylphenylpolysiloxanes, amine-modified silicones, fatty acid-modified silicones, alcohol-modified silicones, alcohol- and fatty acid-modified silicones, polyether group-modified silicones, epoxy-modified silicones, fluoro group-modified silicones, cyclic silicones, alkyl group-modified silicones, etc. In certain aspects, the silicone oil can be selected from the group consisting of aryl silicones, dimethicone copolyols, cyclic structured siloxanes, dimethicones, low molecular weight alkanes, low molecular weight esters, short chain siloxanes, and silicone acrylates. In certain aspects, the silicone oil is a polyorganosiloxane selected from the group consisting of dimethicone, cyclomethicone, polysilicones, phenyl trimethicone, trimethylsilylamodimethicone, stearoxytrimethylsilane, or mixtures of thereof. In other aspects, the silicone oil can be a volatile silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in International Cosmetic Ingredient Dictionary, 11$^{th}$ edition, 2006 as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

The water-in-oil emulsion can also include an emulsifier. A co-emulsifier can also be used. In one embodiment, the emulsifier can be a silicone polyglucoside containing emulsifier. Such an emulsifier can include an octyl radical and/or a sugar glucoside bonded to individual Si—O monomers within the silicone backbone. In particular aspects, the sugar glucoside can be a 6 carbon monosaccharide ranging from 1-8 monomers. The monosaccharides can be bonded together via sugar ether linkages, and the glucoside can be bonded to the silicone backbone via an ethoxy bond. The molecular weight of the silicone polyglucoside emulsifier can be at least 450 daltons. The co-emulsifier can be a glucolipid. The glucolipid can include an alkyl chain. The alkyl chain can vary from 8-20 carbons. The glucose portion of the glucolipid can be a 5 carbon monosaccharide. The alkyl chain can be bonded to the 5 carbon monosaccharide via a sugar ether linkage. The molecular weight of the glucolipid co-emulsifier can be at least 450 daltons. When the silicone polyglucoside emulsifier and glucolipid co-emulsifier are used together, the ratio of the silicone polyglucoside emulsifier to the glucolipid emulsifier can be between about 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, to about 25:1 by total weight of the water-in-oil emulsion. Non-limiting examples of silicone polyglucoside emulsifiers and co-emulsifiers that can be used in the context of the present invention are described in European Patent 612,759 and U.S. Pat. No. 5,831,080, the contents of which are incorporated by reference. Particular emulsifiers include FLUIDINOV™ 20X (available from Seppic, Inc., Fairfield, N.J. (USA)), SPG™ 128 VP (available from Wacker Chemie AG-USA), VSR™ 100 VP (available from Wacker Chemie AG-USA), and Montanov™ emulsifiers 202 (available from Seppic, Inc., Fairfield, N.J. (USA)).

In certain aspects, the viscosity of the water-in-oil inner phase is between 20,000 to 30,000 cps at 25° C. as measured on a Brookfield Viscometer using a TC spindle at 2.5 rpm. However, as explained elsewhere in this specification, the viscosity range can vary inside or outside this range, as desired.

Any standard technique can be used to prepare the water-in-oil inner phase (see, e.g., Sjoblom, 2005; Mollet et al., 2001; *A Guide to Formulating Water-in Silicone Emulsions with Dow Corning 3225C Formulation Aid*, Dow Corning, 1995; Barel et al., *Handbook of Cosmetic Science and Technology*, pp 511-518, 2001). By way of example only, a water-in-oil emulsion can be prepared in a mixing tank and refined and stabilized by passage through a colloid mill or homogenizer. Another non-limiting method includes shaking together the two liquids or by adding one phase drop by drop to the other phase with some form of agitation, such as irradiation by ultrasonic waves of high intensity. Emulsification can also be accomplished by means of emulsifying machines or by other methods known to those of ordinary skill in the art (e.g., the Continental method, the English method, the Bottle Method, or the Beaker method).

C. Preparation of the Three-Phase Emulsion

As mentioned above, a unique aspect of the three-phase emulsion is the manner in which it can be prepared. For instance, and as illustrated in a non-limiting way in the examples section below, the three-phase emulsion can be made by simply mixing the aqueous outer phase with the water-in-oil inner phase (or vice versa) by using any standard mixing procedure. This can be done without using an external heating source. The mixing procedure can include sweeping or slow impeller mixing. Examples of mixing machines that can be used in this process include the Silverson™ homogenizer or a multi-speed Caframo™ mixer. Subsequently, and if desired, high shear mixing can be used (e.g., in one non-limiting aspect, high sheer mixing can include propeller mixing at approximately 1500 to 3000 rpm per one kg of the bulk ingredients). A unique aspect of the mixing procedures is that they can be performed at room temperature (e.g., approximately 25° C.) without heating either the aqueous-gel outer phase or the water-in-oil inner phase prior, during, or after the mixing. Another aspect of the mixing procedure is that the aqueous-gel outer phase can be added to the water-in-oil inner phase prior to or during mixing or the water-in-oil inner phase can be added to the aqueous-gel phase prior to or during mixing.

D. Stability Testing for the Three-Phase Emulsion

A variety of tests can be used to determine if the three-phase emulsion is stable. One example of such a test is a long term stability program at elevated temperatures for twelve (12) weeks with assessments for instability (e.g., check for phase separation of the emulsion) at four (4) week intervals. The use of a texture analyzer can also be used to measure the rheological properties of the emulsion. Micrographs at a magnification of 400× can be taken at twelve (12) weeks to look for coalescence. The same types of assays can also be used to test the stability of the two-phase emulsions of the present invention.

E. Additional Ingredients

Emulsions of the present invention can include additional ingredients. Non-limiting examples of additional ingredients include cosmetic ingredients and pharmaceutical active ingredients.

1. Cosmetic Ingredients

The CTFA International Cosmetic Ingredient Dictionary and Handbook (2006) describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, co-emulsifiers, stabilizers, lubricants, solvents, moisturizers (including, e.g., emollients, humectants, film formers, occlusive agents, and agents that affect the natural moisturization mechanisms of the skin), water-repellants, UV absorbers (physical and chemical absorbers such as titanium dioxide, zinc oxide, avobenzone, octocrylene, benzophenone, etc.), essential oils, vitamins (e.g. A, B, C, D, E, and K), trace metals (e.g. zinc, calcium and selenium), anti-irritants (e.g. steroids and non-steroidal anti-inflammatories), botanical extracts (e.g. aloe vera, chamomile, cucumber extract, ginkgo biloba, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., glycerin, propylene glycol, butylene glycol, pentylene glycol, sorbitol, urea, and manitol), exfoliants (e.g., alpha-hydroxyacids, and beta-hydroxyacids such as lactic acid, glycolic acid, and salicylic acid; and salts thereof) waterproofing agents (e.g., magnesium/aluminum hydroxide stearate), skin conditioning agents (e.g., aloe extracts, allantoin, bisabolol, ceramides, dimethicone, hyaluronic acid, and dipotassium glycyrrhizate). Non-limiting examples of some of these ingredients are provided in the following subsections.

a. Co-Emulsifiers

Emulsions of the present invention can also include a co-emulsifier. A co-emulsifier can include surfactants that can be used in combination with the emulsifiers disclosed in the present invention to form stable emulsions. Non-limiting examples of surfactants that can be used include nonionic, cationic, anionic, and zwitterionic surfactants (See McCutcheon's (1986); U.S. Pat. Nos. 5,011,681; 4,421,769; 3,755,560). For instance, examples of co-emulsifiers include esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof (See International Cosmetic Ingredient Dictionary, 11$^{th}$ Ed., 2006).

b. Stabilizers

Emulsions of the present invention can also include a stabilization agent. Stabilization agents can be an ingredient that aids in stabilizing emulsions or compositions of the present invention. Non-limiting examples of stabilization agents include those known to a person of ordinary skill in the art (see, e.g., International Cosmetic Ingredient Dictionary, 11$^{th}$ Ed., 2006) and those disclose throughout the specification. Examples include hydrogenated castor oil, plant waxes (e.g., beeswax and carnauba wax, etc.), stearic acid, magnesium stearate, aluminum stearate, hydrophobic silicas, polyethylene glycol-alkyl glycol copolymers, mineral waxes, etc.

However, it is noted that stabilization agents are not required in the context of the present invention to obtain a stable water-in-oil emulsion or a stable three-phase emulsion. Indeed, as described above, in some embodiments the stable water-in-oil emulsions or stable three-phase emulsions of the present invention do not include stabilization agents.

c. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal, chlorophensin, Chlorohexedine Digluconate, DMDM Hydantion, Iodopropylbutylcarbamate, Hexetidine, Dichlorobenzyl Alcohol, Methyldibromoglutaronitrile or combinations thereof.

d. Moisturizers

Non-limiting examples of moisturizing agents that can be used with the compositions of the present invention can be found in the International Cosmetic Ingredient Dictionary, 11$^{th}$ Ed., 2006. Examples include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

e. Emollients

Non-limiting examples of emollients include, but are not limited to, vegetable oils, mineral oils, silicone oils, synthetic and natural waxes, medium chain triglycerides, petrolatum, lanolin, aluminum magnesium hydroxide stearate (which can also function as a water repellent), and fatty acid esters. Non-limiting examples of vegetable oils include safflower oil, corn oil, sunflower seed oil, and olive oil.

f. Antioxidants

Non-limiting examples of antioxidants include, but are not limited to, acetyl cysteine, ascorbic acid, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

g. Colorants

In certain non-limiting aspects, the guar gum containing compounds can be used to efficiently disperse colorants throughout a composition and/or a phase (e.g., water, oil, silicone phase) of the composition. Non-limiting examples of colorants that can be used in the context of the present invention include those known to a person of ordinary skill in the art (see, e.g., CTFA International Cosmetic Ingredient Dictionary and Handbook (2006)). For instance natural and synthetic pigments and lakes can be used. Examples of groups of pigments include carbon, cadmium, iron oxide, Prussian blue, chromium, cobalt, copper, titanium, ultramarine, zinc, clay earth, and organic pigments. Specific non-limiting examples of colorants include Aluminum Powder, Blue 1 Lake, Bronze Powder, Chromium Oxide Greens, Copper Powder, Ext. Yellow 7 Lake, Green 3 Lake, Orange 4 Lake, Orange 5 Lake, Orange 10 Lake, Pigment Blue 15, Pigment Blue 15:2, Pigment green 7, Pigment Orange 5, Pigment Red 4, Pigment Red 5, Pigment Red 48, Pigment Red 53, Pigment Red 53:1, Pigment Red 57, Pigment Red 57:1, Pigment Red 63:1, Pigment Red 64:1, Pigment Red 68, Pigment Red 83, Pigment Red 88, Pigment Red 90:1 Aluminum Lake, Pigment Red 112, Pigment Red 172 Aluminum Lake, Pigment Red 173 Aluminum Lake, Pigment Red 190, Pigment Violet 19, Pigment Yellow 1, Pigment Yellow 3, Pigment Yellow 12, Pigment Yellow 13, Pigment Yellow 73, Red 4 Lake, Red 6 Lake, Red 7 Lake, Red 21 Lake, Red 22 Lake, Red 27 Lake, Red 28 Lake, Red 30 Lake, Red 31 Lake, Red 33 Lake, Red 34 Lake, Red 36 Lake, Red 40 Lake, Sunset Yellow Aluminum Lake, Yellow 5 Lake, Yellow 6 Lake, Yellow 7 Lake, Yellow 10 Lake, and Zinc Oxide.

2. Pharmaceutical Active Agents

Pharmaceutical active agents are also contemplated as being useful with the emulsion compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

F. Amount of Ingredients

A person of ordinary skill would recognize that the three-phase emulsions of the present invention can include any number of combinations of ingredients identified above and throughout this specification (e.g., aqueous-gel outer phase, ingredients within aqueous-gel outer phase, water-in-oil inner phase, ingredients within water-in-oil inner phase, etc.) discussed throughout this specification. The concentrations of the ingredients can vary. In non-limiting embodiments, for example, the emulsion compositions may include in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or more, or any range or integer derivable therein, of at least one of the ingredients mentioned throughout the specification and claims. In non-limiting aspects, the percentage of the ingredients can be calculated by weight or volume of the total weight of the three-phase emulsion, of the aqueous-gel outer phase of the emulsion, of the water-in-oil inner phase of the emulsion, of a cosmetic or pharmaceutical composition that includes the emulsion, etc. A person of ordinary skill in the art would understand that the concentrations can vary depending on the desired effect of the emulsions and/or on the product into which the emulsion is incorporated into.

G. Equivalents

Known and unknown equivalents to the ingredients discussed throughout this specification can be used with the emulsion compositions and methods of the present invention. The equivalents can be used as substitutes for the ingredients. The equivalents can also be used to add to the methods and emulsions of the present invention. A person of ordinary skill in the art would be able to recognize and identify acceptable known and unknown equivalents to the ingredients without undue experimentation.

H. Products

The emulsions of the present invention can be incorporated into products. Non-limiting examples of products include cosmetic products, food-based products, pharmaceutical products, etc. By way of example only, non-limiting cosmetic products include sunscreen products, sunless skin tanning products, hair products, fingernail products, moisturizing creams, skin benefit creams and lotions, softeners, day lotions, gels, ointments, foundations, night creams, lipsticks, mascaras, eyeshadows, eyeliners, cheek colors, cleansers, toners, masks, or other known cosmetic products or applications. Additionally, the cosmetic products can be formulated as leave-on or rinse-off products.

I. Kits

Kits are also contemplated as being used in certain aspects of the present invention. For instance, an emulsion of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of an emulsion. In other embodiments, the container can be squeezed (e.g., metal, laminate, or plastic tube) to dispense a desired amount of the emulsion. The emulsion can be dispensed as a spray, an aerosol, a liquid, a fluid, or a semi-solid. The containers can have spray, pump, or squeeze mechanisms. A kit can also include instructions for using the kit and/or emulsion. Instructions can include an explanation of how to apply, use, and maintain the emulsions

EXAMPLES

The following examples are included to demonstrate certain non-limiting aspects of the invention. It should be appreciated by those of skill in the art that the techniques disclosed in the examples which follow representative techniques discovered by the inventor to function well in the practice of the invention. However, those of skill in the art should appreciate that changes can be made in the specific embodiments which are disclosed and still obtain a like or similar result without departing from the spirit and scope of the invention.

Example 1

Water-in-Oil Inner Phase

A non-limiting example of a water-in-silicone emulsion that can be used as the water-in-oil inner phase of the three phase emulsion is illustrated in Table 1.

TABLE 1

| Phase* | Ingredient | % | Grams |
|---|---|---|---|
| A | Cyclomethicone | 4.5 | 180 |
|  | Dimethicone 1.5 cst | 5.5 | 220 |
|  | Diethylhexyl Carbonate | 0.3 | 12 |
|  | Ethyltrisiloxane | 1.0 | 40 |
|  | Silica ethylene methacrylate Copolymer, ITT | 2.0 | 80 |
|  | Cyclomethicone and Caprylyl Dimethicone ethoxy Glucoside | 10.00 | 400 |
|  | Cyclomethicone and Dimethiconol | 1.0 | 40 |
|  | Neopentyl Glycol Heptanoate | 1.0 | 40 |
|  | Octyldodecanol and Octyldodecyl Xyloside | 2.0 | 80 |
|  | Talc | 12.5 | 500 |
| B | Cyclomethicone and Dimethicone/Vinyltrimethoxysilicate | 3.0 | 120 |
|  | Jojoba Esters | 0.5 | 20 |
| C | Cyclomethicone and PEG 10 Dimethicone and Distearimonium Hectorite | 2.0 | 80 |
|  | Silicone Acrylate | 2.0 | 80 |
| D | Water(Deionized) | 47.20 | 1888 |
|  | Niacinamide | 1.00 | 40 |
| E | Glycerin | 2.5 | 100 |
|  | Pentylene Glycol | 1.0 | 40 |
| F | Preservative | 1.0 | 40 |
|  | TOTAL | 100.0000 | 4000.0000 |

*Phases A-C include the silicone oil phase of the water-in-silicone emulsion. Phases D-F include the dispersed water phase.

The water-in-silicone emulsion in Table 1 was prepared as follows: Added Phase A compounds in order into a vessel and mixed with a 3 blade propeller at 425 rpm. On addition of the silica the phase thickened temporarily. Used a sweep or Z bar to disperse the silica throughout the phase until the batch resembled a uniform liquid. Added remainder of Phase A and mixed with propeller until uniform. Adjusted the speed of the mixer as needed to avoid splashing, but good movement of the batch. Added Phase B dry mix (powders or pigments) and allowed the batch to "wet" the solids until dispersed evenly through out the batch. Adjusted the speed of the mixer to accommodate the additional solids. Added Phase C, mixed with propeller and homogenized for at least 5 minutes at 2000 rpm. Confirmed batch contained no agglomerations or undispersed powder. Discontinued homogenizer and switched back to propeller mixing. Added Phase D to the main vessel. Mixed until uniform again. In a separate vessel, weighed out Phase E ingredients. In a separate vessel added in specific order (pentylene glycol, glycerin, then preservative). When adding each material mixed until transparent. The liquid initially appeared opaque, but after mixing the solution became clear. Added this to the Phase E material and mixed until transparent. Meter dosed (using a metering pump or dosing equipment, such as a separatory funnel) the water phase to the silicone phase at a rate such that the water phase is added in 30 minutes with moderate to high speed mixing (500-700 rpm—Caframo). Continued mixing at this speed for the time taken to add the water phase. Switched to a homogenizer and mixed at 1 kg of bulk/minute (i.e., a 10 kg batch will mix for 10 minutes at 2000 rpm.). Transferred batch to holding vessel.

The water-in-silicone emulsion had a viscosity of 30,000 cps on a Brookfield Viscometer Model RVT with Gyroscope using a T spindle C at 2.5 rpm at 25° C.

Example 2

Aqueous-Gel Outer Phase

A non-limiting example of an aqueous-gel outer phase that can be used as the aqueous-gel outer phase of the three phase emulsion is illustrated in Table 2.

TABLE 2

| Phase* | Ingredient | % Concentration (by weight) |
|---|---|---|
| A | Deionized Water | 91.0 |
|  | Ascorbyl Glucoside | 3.0 |
|  | Polyacrylate 13, Polyisobutene, Polysorbate 20 | 3.2 |
|  | Hydroxyethyl acetate/Sodium Acryldimethyl taurate copolymer, Squalane, Polysorbate 60, Sorbitan Isostearate | 1.8 |
|  | Preservative | 1.0 |
|  | TOTAL | 100 |

*Phase A is the aqueous-gel outer phase.

Added each ingredient to a vessel under high shear mixing by using a rotation speed of 1000-3000 rpm with a Greerco Lab scale homogenizer based on 1 kg of bulk per minute creating a high turnover of batch volume. The batch thickened as each of the emulsifiers were added. Homogenized the batch an additional 2-4 minutes to yield a uniform cream gel like appearance. The aqueous-gel outer phase had a viscosity of approximately 100,000 to 140,000 cps on a Brookfield Viscometer Model RVT with Gyroscope using a T spindle C at 2.5 rpm at 25° C.

Example 3

Method of Preparing the Three-Phase Emulsion and Stability Data

Non-limiting examples of how two three-phased emulsions (see FIGS. 1 and 2) of the present invention were prepared by using the water-in-silicone emulsion of Table 1 and the aqueous-gel outer phase of Table 2 is provided below.

In a suitable vessel measure the appropriate ratios of primary and secondary phases such that they add to 100. In the present case, two separate three-phase emulsions were prepared with different ratios (see FIGS. 1 and 2). Using either propeller or high shear mixing, add the phases together without heat (i.e., this reaction is exothermic). Mix until the mixture takes on a uniform appearance without agglomeration or streaks of primary phase with in the secondary phase. Once complete, transfer to a holding vessel.

Figure 2:
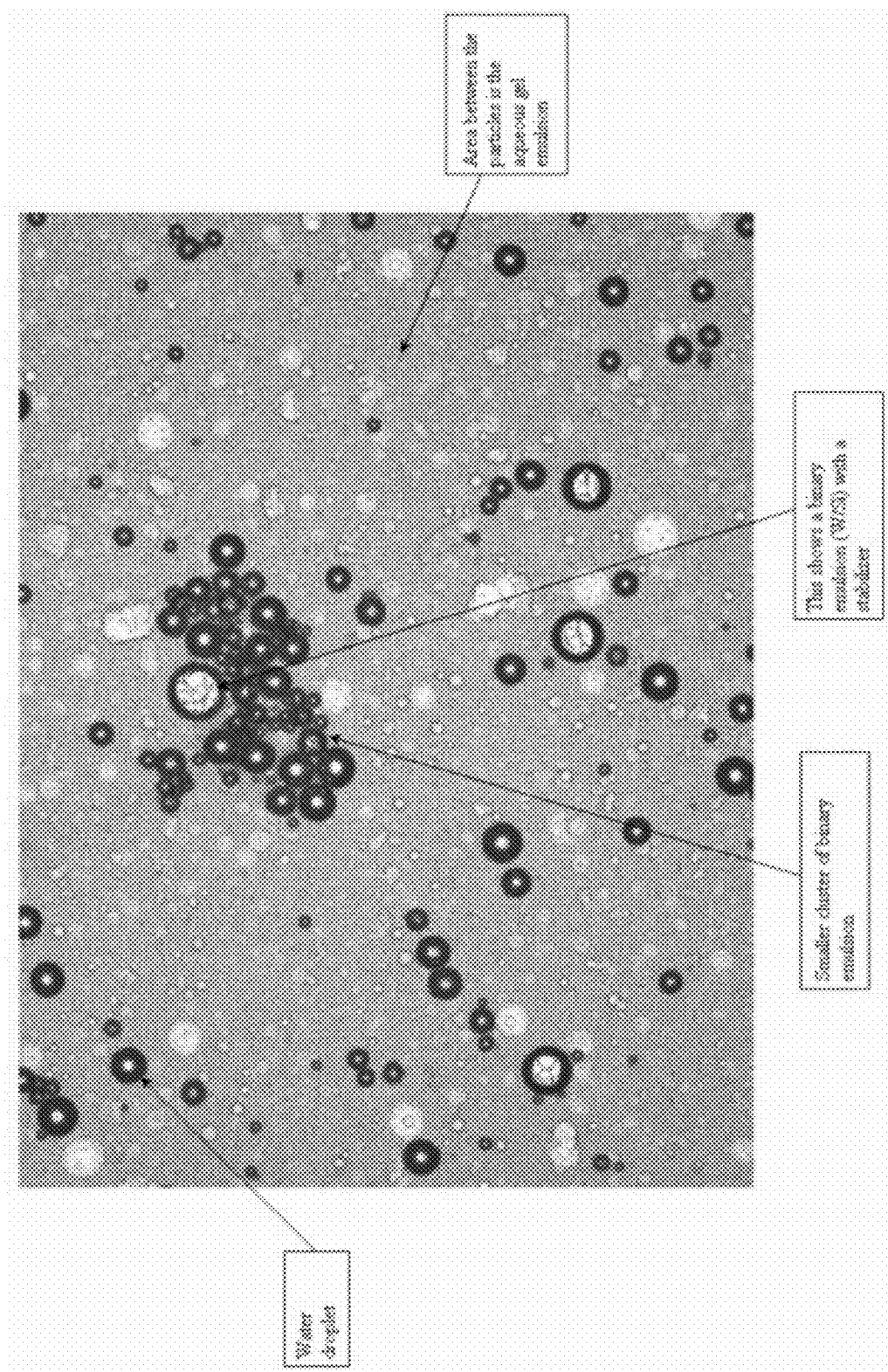
FIG. 2 is a micrograph of a three-phase emulsion of the present invention. The water-in-oil phase (referred to as "primary phase") includes 50.0% by weight of the total weight of the emulsion. The aqueous-gel outer phase (referred to as "secondary phase") include 50.0% by weight of the total weight of the emulsion.

FIG. 1 is a micrograph of a stable three-phase emulsion which includes 92.5% by weight of the water-in-silicone emulsion of Table 1 based on the total weight of the emulsion and 7.5% by weight of the aqueous-gel phase of Table 2 based on the total weight of the emulsion. FIG. 2 is a micrograph of a stable three-phase emulsion which includes 50.0% by weight of the water-in-silicone emulsion of Table 1 based on the total weight of the emulsion and 50.0% by weight of the aqueous-gel phase of Table 2 based on the total weight of the emulsion.

The stability of the three-phase emulsions were determined by using the following assay. The emulsions corresponding to FIGS. 1 and 2 were placed in 2 oz and 16 oz jars and stored at various temperatures (25° C., 38° C., and 45° C.) and subjected to a freeze thaw cycle test for a week (5 cycles). A ruggedness/shake test was also performed to assess emulsion integrity. At 4 week intervals the 25° C., 38° C., and 45° C. samples were removed and allowed to equilibrate back to room temperature and then assessed for color, odor, appearance, and viscosity changes. Three 4 week intervals were performed. The micrographs of FIGS. 1 and 2 correspond to the 25° C. sample, which confirm the stability of these emulsions. These micrographs show micelles with stabilized primary phase between the gelled secondary phase. The 38° C. and 45° C. samples were also confirmed to be stable (data not shown).

Stability of the three-phase emulsions were also determined by using a color change assay. In this test, ascorbic acid was placed in the aqueous-gel outer phase and niacinamide was placed in the water phase of the water-in-oil-inner phase. A yellow color will be seen if ascorbic acid interacts with niacinamide (i.e., if the aqueous-gel outer phase interacts with the water phase of the water-in-oil inner phase). A yellow color was not observed.

Example 4

Foundation Formula 92.5/7.5

A non-limiting example of a foundation formula that includes a stable three-phase emulsion of the present invention is illustrated in Table 3. This emulsion includes a water-in-silicone internal phase at 92.5% by weight of the total weight of the emulsion and an aqueous-gel outer phase at 7.5% by weight of the total weight of the emulsion.

TABLE 3

|   | Ingredient | Quantity % (Individual Phases) | Mass (g) (Individual Phases) | Mass (g) (3-Phase Emulsion) |
|---|---|---|---|---|
| W/S Phase* | | | | |
| A | Cyclopentasiloxane (Low D4) | 4.50 | 45.00 | 41.625 |
|   | Dimethicone 200 1.5 cst | 5.50 | 55.00 | 50.875 |
|   | Ethyltrisiloxane | 1.00 | 10.00 | 9.25 |
|   | Diethylhexyl Carbonate | 0.30 | 3.00 | 2.775 |
|   | Silica + Ethylene Methacrylate Copolymer + Isopropyl Titanium Triostearate (ITT) | 2.00 | 20.00 | 18.50 |
|   | D5 + Capryl Dimethicone Ethoxy Glucoside | 10.00 | 100.00 | 92.5 |
|   | Dimethiconol | 1.00 | 10.00 | 9.25 |
|   | Neopentyl Diglycol Heptanoate | 1.00 | 10.00 | 9.25 |
|   | Octyldodecanol + Octyldodecyl Xyloside | 2.00 | 20.00 | 18.50 |
| B | Talc/Pigment | 12.5 | 125.00 | 115.625 |
| C | D5 + Dimethicone/ Vinyltrimethoxysilicate Crosspolymer | 3.00 | 30.00 | 27.75 |
|   | Jojoba Esters | 0.50 | 5.00 | 4.625 |
|   | D5 + PEG 10 Dimethicone + Distearimonium Hectorite | 2.00 | 20.00 | 18.50 |
| D | Silicone Acrylate | 2.00 | 20.00 | 18.50 |
| E | Water (Deionized) | 47.20 | 472.00 | 436.60 |
|   | Niacinamide (B6) | 1.00 | 10.00 | 9.25 |
| F | Pentylene Glycol | 1.00 | 10.00 | 9.25 |
|   | Glycerin | 2.50 | 25.00 | 23.125 |
| G | Germaben II | 1.00 | 10.00 | 9.25 |
|   |   | 100.00 | 1000.00 | 925.00 |
| Gel Phase** | | | | |
| A | Water | 91.00 | 910.00 | 68.25 |
| B | Ascorbyl Glucoside | 3.00 | 30.00 | 2.25 |
|   | Hydroxyethyl Acetate + Sodium Acryldimethyl Taurate Copolymer + Squalane + Polysorbate 60 + Sorbitan Isostearate | 1.80 | 18.00 | 1.35 |
| C | Polyacrylate 13 + Polyisobutene + Polysorbate 20 | 3.20 | 32.00 | 2.40 |
| D | Germaben II | 1.00 | 10.00 | 0.75 |
|   |   | 100.00 | 1000.00 | 75.00 |

*"WS" refers to the internal water-in-silicone inner phase.
**"Gel Phase refers to the aqueous gel outer phase The water-in-silicone emulsion in Table 3 was prepared as follows: Added Phase A compounds in order into a vessel and mixed with a 3 blade propeller at 425 rpm. On addition of the silica the phase thickened temporarily. Used a sweep or Z bar to disperse the silica throughout the phase until the batch resembled a uniform liquid. Added remainder of Phase A and mixed with propeller until uniform. Adjusted the speed of the mixer as needed to avoid splashing, but good movement of the batch. Added Phase B dry mix (powders or pigments) and allowed the batch to "wet" the solids until dispersed evenly through out the batch. Adjusted the speed of the mixer to accommodate the additional solids. Added Phase C, mixed with propeller and homogenized for at least 5 minutes at 2000 rpm. Confirmed batch contained no agglomerations or undispersed powder. Discontinued homogenizer and switched back to propeller mixing. Added Phase D to the main vessel. Mixed until uniform again. In a separate vessel, weighed out Phase E ingredients. In a separate vessel added in specific order (pentylene glycol, glycerin, then preservative). When adding each material mixed until transparent. The liquid initially appeared opaque, but after mixing the solution became clear. Added this to the Phase E material and mixed until transparent. Meter dosed (using a metering pump or dosing equipment, such as a separatory funnel) the water phase to the silicone phase at a rate such that the water phase is added in 30 minutes with moderate to high speed mixing (500-700 rpm—Caframo). Continued mixing at this speed for the time taken to add the water phase. Switched to a homogenizer and mixed at 1 kg of bulk/minute (i.e., a 10 kg batch will mix for 10 minutes at 2000 rpm.). Transferred batch to holding vessel. The water-in-silicone emulsion had a viscosity of 30,000 cps on a Brookfield Viscometer Model RVT with Gyroscope using a T spindle C at 2.5 rpm at 25° C.

The gel phase in Table 3 was prepared as follows: Added each ingredient to a vessel under high shear mixing by using a rotation speed of 1000-3000 rpm with a Greerco Lab scale homogenizer based on 1 kg of bulk per minute creating a high turnover of batch volume. The batch thickened as each of the emulsifiers were added. Homogenized the batch an additional 2-4 minutes to yield a uniform cream gel like appearance. The aqueous-gel outer phase had a viscosity of approximately 100,000 to 140,000 cps on a Brookfield Viscometer Model RVT with Gyroscope using a T spindle C at 2.5 rpm at 25° C.

The three-phase emulsion in Table 3 was prepared in the manner described in Example 3.

Figure 3:
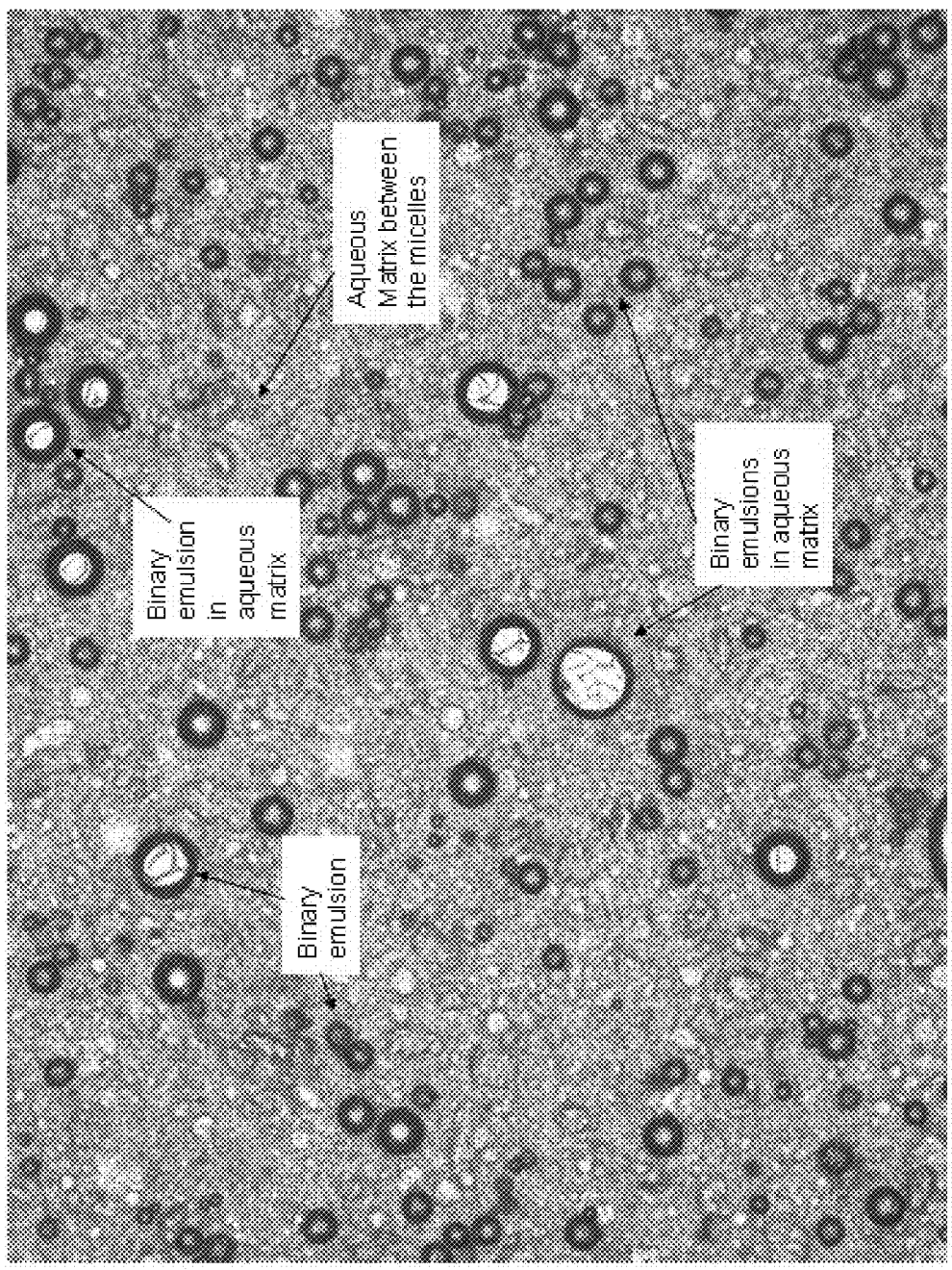
FIG. 3 is a micrograph of a three-phase emulsion of the present invention. The water-in-oil phase includes 92.5% by weight of the total weight of the emulsion. The aqueous-gel outer phase includes 7.5% by weight of the total weight of the emulsion. The micrograph was taken approximately 24 hours after the three-phase emulsion was prepared. The temperature of the three-phase emulsion was room temperature (approximately 20° C. to 25° C.).
Figure 4:
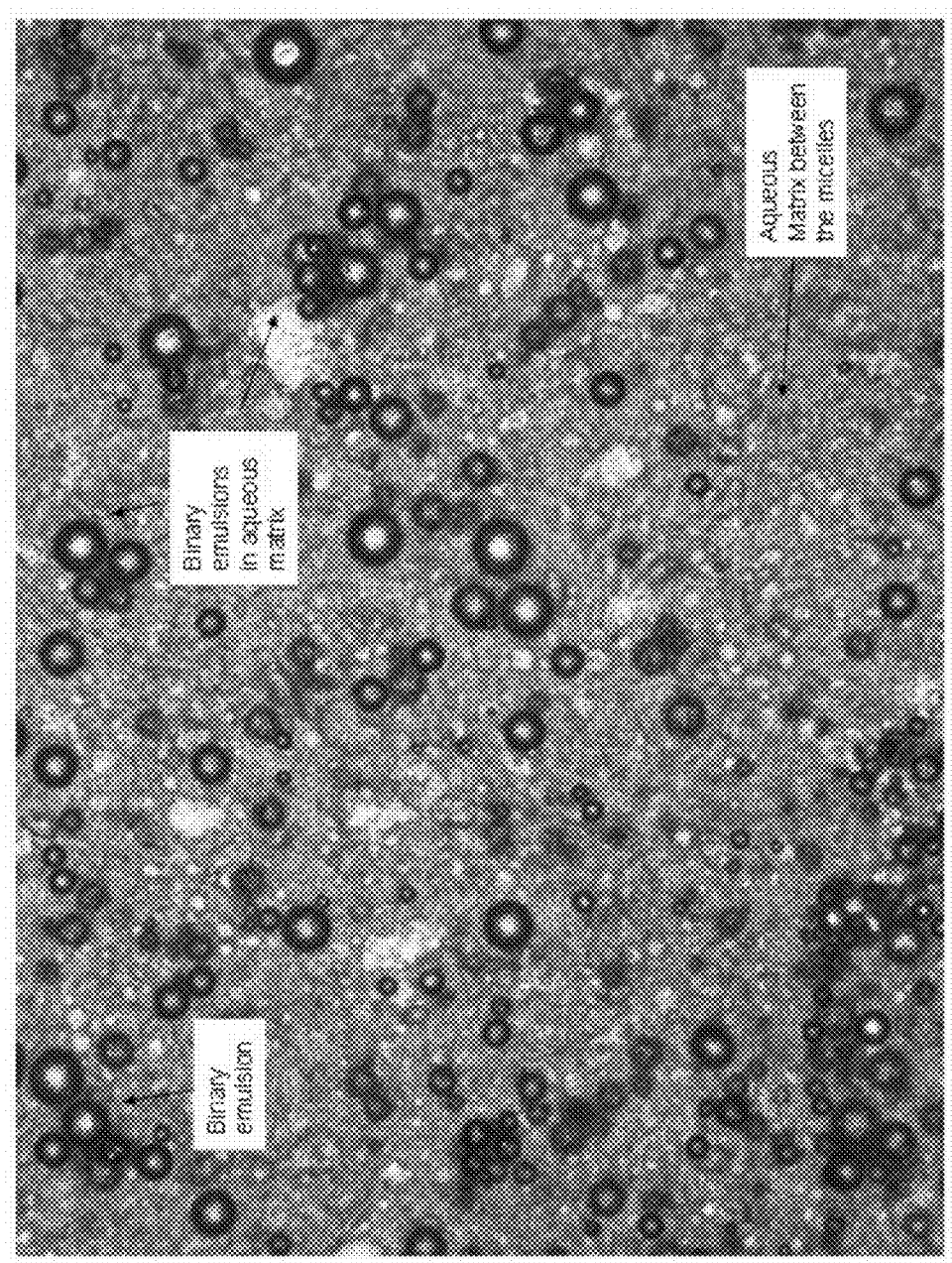
FIG. 4 is a micrograph of the three-phase emulsion referenced in FIG. 3. The micrograph was taken after the three-phase emulsion was stored for four weeks at 45° C.

FIG. 3 is a micrograph of the three-phase emulsion in Table 3. The micrograph was taken approximately 24 hours after the three-phase emulsion was prepared. The temperature of the three-phase emulsion was room temperature (approximately 20° C. to 25° C.). The three-phase emulsion was subsequently stored for four weeks at 45° C. in a 2 oz and 16 oz jar undisturbed in a temperature and humidity controlled chamber. These storage conditions are used to replicate the storage of a given composition at room temperature for one-year. FIG. 4 is a micrograph of the three-phase emulsion confirming its stability. These data show that the three-phase emulsion in Table 3 is storage stable at room temperature for at least one year by the presence of the binary emulsions remaining within the aqueous gel matrix.

Stability of the three-phase emulsion in Table 3 was also determined by using a color change assay. In this test, ascorbyl palmitate was placed in the aqueous-gel outer phase and niacinamide (B6) was placed in the water phase of the water-in-oil-inner phase. A yellow color will be seen if ascorbyl palmitate interacts with niacinamide (i.e., if the aqueous-gel outer phase interacts with the water phase of the water-in-oil inner phase). A yellow color was not observed after four weeks of storage at 45° C.

Example 5

Foundation Formula 75/25

A non-limiting example of a foundation formula that includes a stable three-phase emulsion of the present invention is illustrated in Table 4. This emulsion includes a water-in-silicone internal phase at 75.0% by weight of the total weight of the emulsion and an aqueous-gel outer phase at 25.0% by weight of the total weight of the emulsion.

TABLE 4

| | Ingredient | Quantity % (Individual Phases) | Mass (g) (Individual Phases) | Mass (g) (3-Phase Emulsion) |
|---|---|---|---|---|
| W/S Phase* | | | | |
| A | Cyclopentasiloxane (Low D4) | 4.50 | 45.00 | 41.625 |
| | Dimethicone 200 1.5 cst | 5.50 | 55.00 | 50.875 |
| | Ethyltrisiloxane | 1.00 | 10.00 | 7.25 |
| | Diethylhexyl Carbonate | 0.30 | 3.00 | 2.25 |
| | Silica + Ethylene Methacrylate Copolymer + Isopropyl Titanium Triostearate (ITT) | 2.00 | 20.00 | 15.00 |
| | D5 + Capryl Dimethicone Ethoxy Glucoside | 10.00 | 100.00 | 75.0 |
| | Dimethiconol | 1.00 | 10.00 | 7.50 |
| | Neopentyl Diglycol Heptanoate | 1.00 | 10.00 | 7.50 |
| | Octyldodecanol + Octyldodecyl Xyloside | 2.00 | 20.00 | 15.00 |

TABLE 4-continued

| | Ingredient | Quantity % (Individual Phases) | Mass (g) (Individual Phases) | Mass (g) (3-Phase Emulsion) |
|---|---|---|---|---|
| B | Talc/Pigment | 12.5 | 125.00 | 93.75 |
| C | D5 + Dimethicone/ Vinyltrimethoxysilicate Crosspolymer | 3.00 | 30.00 | 22.50 |
| | Jojoba Esters | 0.50 | 5.00 | 3.75 |
| | D5 + PEG 10 Dimethicone + Distearimonium Hectorite | 2.00 | 20.00 | 15.0 |
| D | Silicone Acrylate | 2.00 | 20.00 | 15.0 |
| E | Water (Deionized) | 47.20 | 472.00 | 354.0 |
| | Niacinamide (B6) | 1.00 | 10.00 | 7.50 |
| F | Pentylene Glycol | 1.00 | 10.00 | 7.50 |
| | Glycerin | 2.50 | 25.00 | 18.75 |
| G | Germaben II | 1.00 | 10.00 | 7.50 |
| | | 100.00 | 1000.00 | 750.00 |
| Gel Phase** | | | | |
| A | Water | 91.00 | 910.00 | 227.50 |
| | Ascorbyl Glucoside | 3.00 | 30.00 | 7.50 |
| B | Hydroxyethyl Acetate + Sodium Acryldimethyl Taurate Copolymer + Squalane + Polysorbate 60 + Sorbitan Isostearate | 1.80 | 18.00 | 4.50 |
| C | Polyacrylate 13 + Polyisobutene + Polysorbate 20 | 3.20 | 32.00 | 8.00 |
| D | Germaben II | 1.00 | 10.00 | 2.50 |
| | | 100.00 | 1000.00 | 250.00 |

*"WS" refers to the internal water-in-silicone inner phase.
**"Gel Phase refers to the aqueous gel outer phase The water-in-silicone emulsion in Table 4 was prepared as follows: Added Phase A compounds in order into a vessel and mixed with a 3 blade propeller at 425 rpm. On addition of the silica the phase thickened temporarily. Used a sweep or Z bar to disperse the silica throughout the phase until the batch resembled a uniform liquid. Added remainder of Phase A and mixed with propeller until uniform. Adjusted the speed of the mixer as needed to avoid splashing, but good movement of the batch. Added Phase B dry mix (powders or pigments) and allowed the batch to "wet" the solids until dispersed evenly through out the batch. Adjusted the speed of the mixer to accommodate the additional solids. Added Phase C, mixed with propeller and homogenized for at least 5 minutes at 2000 rpm. Confirmed batch contained no agglomerations or undispersed powder. Discontinued homogenizer and switched back to propeller mixing. Added Phase D to the main vessel. Mixed until uniform again. In a separate vessel, weighed out Phase E ingredients. In a separate vessel added in specific order (pentylene glycol, glycerin, then preservative). When adding each material mixed until transparent. The liquid initially appeared opaque, but after mixing the solution became clear. Added this to the Phase E material and mixed until transparent. Meter dosed (using a metering pump or dosing equipment, such as a separatory funnel) the water phase to the silicone phase at a rate such that the water phase is added in 30 minutes with moderate to high speed mixing (500-700 rpm—Caframo). Continued mixing at this speed for the time taken to add the water phase. Switched to a homogenizer and mixed at 1 kg of bulk/minute (i.e., a 10 kg batch will mix for 10 minutes at 2000 rpm.). Transferred batch to holding vessel. The water-in-silicone emulsion had a viscosity of 30,000 cps on a Brookfield Viscometer Model RVT with Gyroscope using a T spindle C at 2.5 rpm at 25° C.

The gel phase in Table 4 was prepared as follows: Added each ingredient to a vessel under high shear mixing by using a rotation speed of 1000-3000 rpm with a Greerco Lab scale homogenizer based on 1 kg of bulk per minute creating a high turnover of batch volume. The batch thickened as each of the emulsifiers were added. Homogenized the batch an additional 2-4 minutes to yield a uniform cream gel like appearance. The aqueous-gel outer phase had a viscosity of approximately 100,000 to 140,000 cps on a Brookfield Viscometer Model RVT with Gyroscope using a T spindle C at 2.5 rpm at 25° C.

The three-phase emulsion in Table 4 was prepared in the manner described in Example 3.

Figure 5:
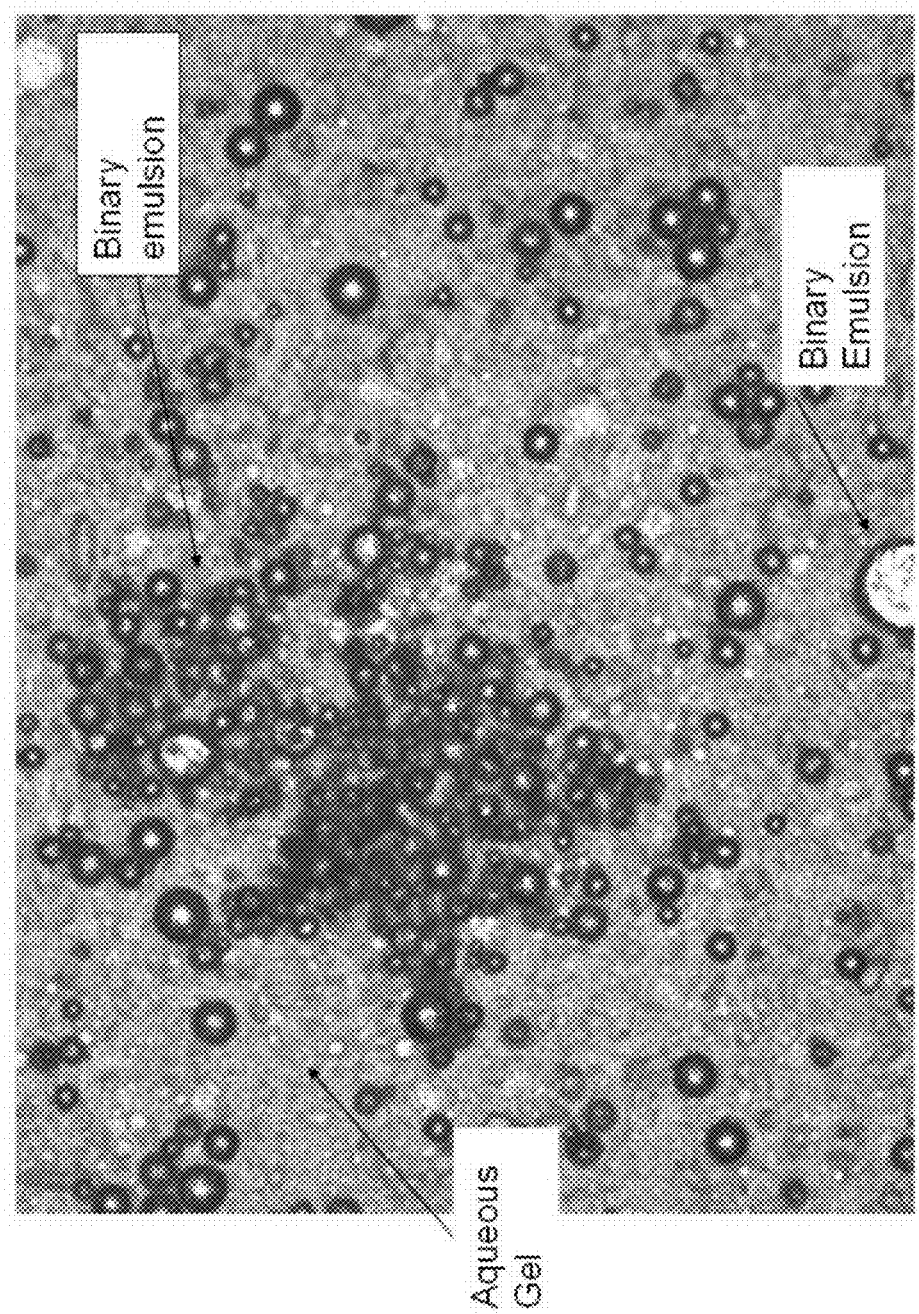
FIG. 5 is a micrograph of a three-phase emulsion of the present invention. The water-in-oil phase includes 75.0% by weight of the total weight of the emulsion. The aqueous-gel outer phase includes 25.0% by weight of the total weight of the emulsion. The micrograph was taken approximately 24 hours after the three-phase emulsion was prepared. The temperature of the three-phase emulsion was room temperature (approximately 20° C. to 25° C.).
Figure 6:
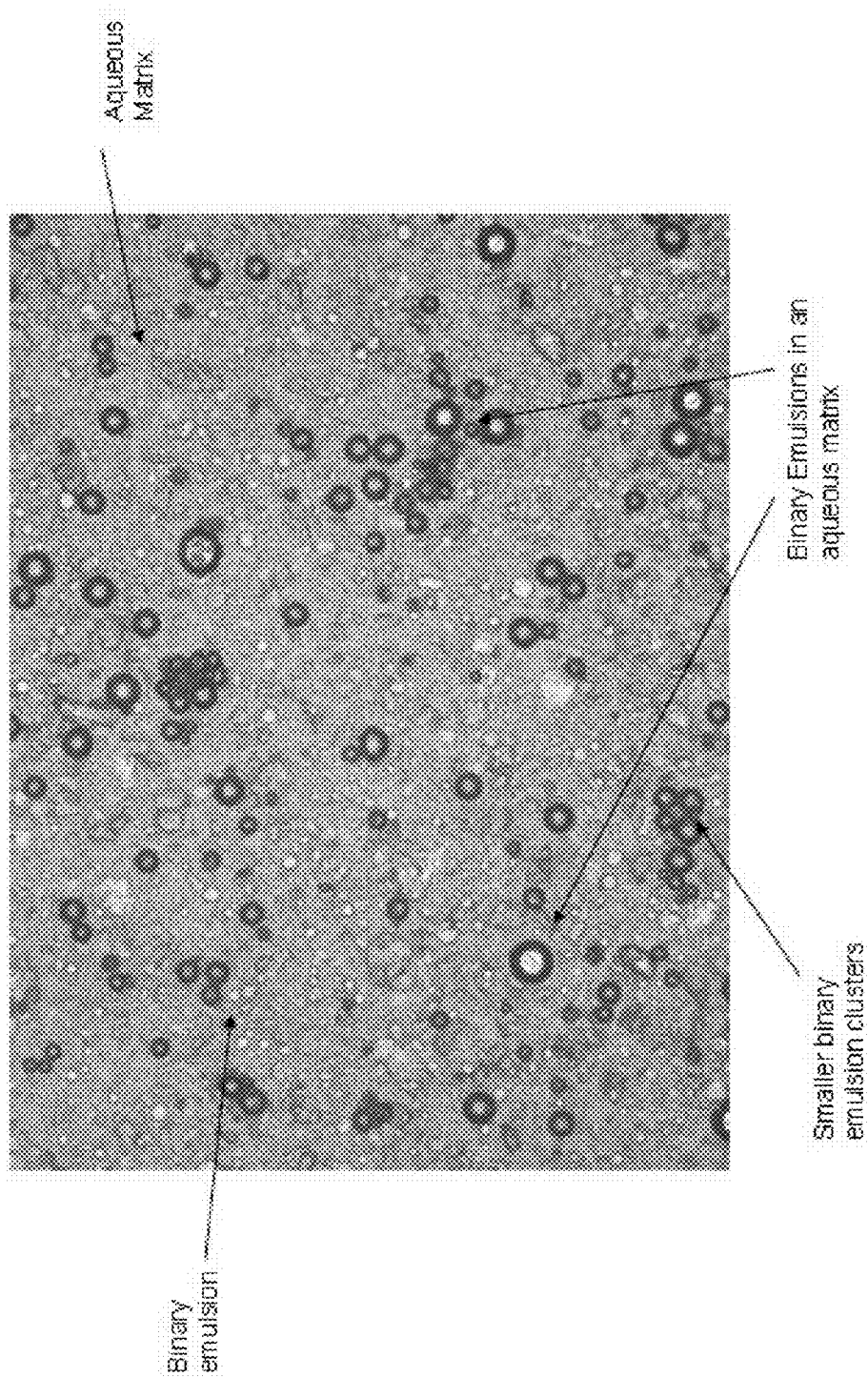
FIG. 6 is a micrograph of the three-phase emulsion referenced in FIG. 5. The micrograph was taken after the three-phase emulsion was stored for four weeks at 45° C.

FIG. 5 is a micrograph of the three-phase emulsion in Table 4. The micrograph was taken approximately 24 hours after the three-phase emulsion was prepared. The temperature of the three-phase emulsion was room temperature (approximately 20° C. to 25° C.). The three-phase emulsion was subsequently stored for four weeks at 45° C. in a _2 oz and 16 oz jar undisturbed in a temperature and humidity controlled chamber. These storage conditions are used to replicate the storage of a given composition at room temperature for one-year. FIG. 6 is a micrograph of the three-phase emulsion confirming its stability. These data show that the three-phase emulsion in Table 4 is storage stable at room temperature for at least one year by the presence of the binary emulsions remaining within the aqueous gel matrix.

Stability of the three-phase emulsion in Table 4 was also determined by using a color change assay. In this test, ascorbyl palmitate was placed in the aqueous-gel outer phase and niacinamide (B6) was placed in the water phase of the water-in-oil-inner phase. A yellow color will be seen if ascorbyl palmitate interacts with niacinamide (i.e., if the aqueous-gel outer phase interacts with the water phase of the water-in-oil inner phase). A yellow color was not observed after four weeks of storage at 45° C.

Example 6

Concealer Formula 50/50

A non-limiting example of a concealer formula that includes a stable three-phase emulsion of the present invention is illustrated in Table 5. This emulsion includes a water-in-silicone internal phase at 50.0% by weight of the total weight of the emulsion and an aqueous-gel outer phase at 50.0% by weight of the total weight of the emulsion.

TABLE 5

| Ingredient | | Quantity % (Individual Phases) | Mass (g) (Individual Phases) | Mass (g) (3-Phase Emulsion) |
|---|---|---|---|---|
| W/S Phase* | | | | |
| A | Cyclopentasiloxane (Low D4) | 4.50 | 45.00 | 22.50 |
| | Cetyl Dimethicone Copolyol + Polyglyceryl 4 Isostearate + Hexyl Laurate | 3.00 | 30.00 | 15.00 |

TABLE 5-continued

| Ingredient | | Quantity % (Individual Phases) | Mass (g) (Individual Phases) | Mass (g) (3-Phase Emulsion) |
|---|---|---|---|---|
| | Cetyl Dimethicone Copolyol | 1.00 | 10.00 | 5.00 |
| | Cetyl Dimethicone | 1.00 | 10.00 | 5.00 |
| | Isononyl Isononanoate | 9.65 | 96.50 | 48.25 |
| | Sorbitan Isostearate | 2.50 | 25.00 | 12.50 |
| | Zinc Oxide | 2.00 | 20.00 | 10.00 |
| | Lauroyl Lysine | 2.00 | 20.00 | 10.00 |
| | PTFE-20 | 1.60 | 16.00 | 8.00 |
| B | TiO$_2$ Dry Mix | 21.104 | 211.04 | 105.52 |
| C | Yellow Iron Oxide - Dry Mix | 3.872 | 38.72 | 19.36 |
| | Red Iron Oxide - Dry Mix | 0.548 | 5.48 | 2.74 |
| | Black Iron Oxide - Dry Mix | 0.476 | 4.76 | 2.38 |
| D | Nylon-12 | 0.20 | 2.00 | 1.00 |
| | Tocopherol Acetate | 0.20 | 2.00 | 1.00 |
| | Retinyl Palmitate | 0.10 | 1.00 | 0.50 |
| | Germaben II | 1.00 | 10.00 | 5.00 |
| E | Bees Wax Sesame Seed Oil | 2.50 | 25.00 | 12.50 |
| F | Water (Deionized) | 39.650 | 396.50 | 198.25 |
| | Sodium Chloride | 0.60 | 6.00 | 3.00 |
| G | Camomile Extract | 1.25 | 12.50 | 6.25 |
| | Hydrolyzed Wheat Protein-Polysilicone | 1.25 | 12.50 | 6.25 |
| | | 100.00 | 1000.00 | 500.00 |
| Gel Phase** | | | | |
| A | Water | 94.00 | 940.00 | 470.00 |
| B | Hydroxyethyl Acetate + Sodium Acryldimethyl Taurate Copolymer + Squalane + Polysorbate 60 + Sorbitan Isostearate | 1.80 | 18.00 | 9 |
| C | Polyacrylate 13 + Polyisobutene + Polysorbate 20 | 3.20 | 32.00 | 16.00 |
| D | Germaben II | 1.00 | 10.00 | 5.00 |
| | | 100.00 | 1000.00 | 500.00 |

*"WS" refers to the internal water-in-silicone inner phase.
**"Gel Phase refers to the aqueous gel outer phase The water-in-silicone emulsion in Table 5 was prepared as follows: Added Phase A compounds in order into a vessel and mixed with a 3 blade propeller at 425 rpm. On addition of the powders the phase thickened temporarily. Used a sweep or Z bar to disperse the powders throughout the phase until the batch resembled a uniform liquid. Added remainder of Phase A and mixed with propeller until uniform. Adjusted the speed of the mixer as needed to avoid splashing, but good movement of the batch. Added Phase B dry mix (powders or pigments) and allowed the batch to "wet" the solids until dispersed evenly through out the batch. Adjusted the speed of the mixer to accommodate the additional solids. Added Phase C, mixed with propeller and homogenized for at least 5 minutes at 2000 rpm. Confirmed batch contained no agglomerations or undispersed powder. Discontinued homogenizer and switched back to propeller mixing. Added Phase D to the main vessel. Mixed until uniform again. Add phase E, ingredients. In a separate vessel add the water and salt until transparent When adding each material mixed until transparent. Once dissolved Meter dosed (using a metering pump or dosing equipment, such as a separatory funnel) the water phase is added to the silicone phase at a rate such that the water phase is added in 30 minutes with moderate to high speed mixing (500-700 rpm—Caframo). Continued mixing at this speed for the time taken to add the water phase. Switched to a homogenizer and mixed at 1 kg of bulk/minute (i.e., a 10 kg batch will mix for 10 minutes at 2000 rpm.). Add phase G and transfer the batch to holding vessel. The water-in-silicone emulsion had a viscosity of 50,000 cps to 120,000 on a Brookfield Viscometer Model RVT with Gyroscope using a T spindle D at 2.5 rpm at 25° C.

The gel phase in Table 5 was prepared as follows: Added each ingredient to a vessel under high shear mixing by using a rotation speed of 1000-3000 rpm with a Greerco Lab scale homogenizer based on 1 kg of bulk per minute creating a high turnover of batch volume. The batch thickened as each of the emulsifiers were added. Homogenized the batch an additional 2-4 minutes to yield a uniform cream gel like appearance. The aqueous-gel outer phase had a viscosity of approximately 100,000 to 140,000 cps on a Brookfield Viscometer Model RVT with Gyroscope using a T spindle C at 2.5 rpm at 25° C.

The three-phase emulsion in Table 5 was prepared in the manner described in Example 3.

Stability of the three-phase emulsion in Table 5 was determined by visual observation which included evaluating the color, odor, appearance, signs of phase separation, texture, application changes, exposure to vigorous mixing (shake test), high temperature exposure (60° C. for 5 days), and Freeze/thaw stability for 5 cycles. The samples were evaluated at 4 week intervals for 12 weeks using samples at 25, 38 and 45° C. The formula past all requirements for stability.

Example 7

Oil-Control Formula 92.5/7.5

A non-limiting example of an oil-control formula that includes a stable three-phase emulsion of the present invention is illustrated in Table 6. This emulsion includes a water-in-silicone internal phase at 92.5% by weight of the total weight of the emulsion and an aqueous-gel outer phase at 7.50% by weight of the total weight of the emulsion.

TABLE 6

| | Ingredient | Quantity % (Individual Phases) | Mass (g) (Individual Phases) | Mass (g) (3-Phase Emulsion) |
|---|---|---|---|---|
| W/S Phase* | | | | |
| A | Cyclopentasiloxane (Low D4) | 5.50 | 55.00 | 50.875 |
| | Dimethicone 200 1.5 cst | 5.50 | 55.00 | 50.875 |
| | Ethyltrisiloxane | 1.00 | 10.00 | 9.25 |
| | Silica + Ethylene Methacrylate Copolymer + Isopropyl Titanium Triostearate (ITT) | 2.00 | 20.00 | 18.50 |
| | D5 + Capryl Dimethicone Ethoxy Glucoside | 10.00 | 100.00 | 92.5 |
| | Dimethiconol | 1.00 | 10.00 | 9.25 |
| | Cetyl PEG 15 + PPG 15 + Butyl Ethyl Dimethicone | 2.00 | 20.00 | 18.50 |

TABLE 6-continued

| | Ingredient | Quantity % (Individual Phases) | Mass (g) (Individual Phases) | Mass (g) (3-Phase Emulsion) |
|---|---|---|---|---|
| | Dimethicone and Dimethicone Crosspolymer | 12.50 | 125.00 | 115.625 |
| C | D5 + Dimethicone/ Vinyltrimethoxysilicate Crosspolymer | 3.00 | 30.00 | 27.75 |
| | Jojoba Esters | 0.50 | 5.00 | 4.625 |
| | D5 + PEG 10 Dimethicone + Distearimonium Hectorite | 2.00 | 20.00 | 18.50 |
| D | Silicone Acrylate | 1.00 | 10.00 | 9.25 |
| E | Water (Deionized) | 47.50 | 475.00 | 439.375 |
| F | Pentylene Glycol | 1.00 | 10.00 | 9.25 |
| | Glycerin | 2.50 | 25.00 | 23.125 |
| G | Dimethicone/Vinyl Dimethicone Crosspolymer + $C_{12-14}$ Pareth-12 | 2.00 | 20.00 | 18.50 |
| | Germaben II | 1.00 | 10.00 | 9.25 |
| | | 100.00 | 1000.00 | 925.00 |
| Gel Phase** | | | | |
| A | Water | 94.00 | 940.00 | 70.50 |
| B | Hydroxyethyl Acetate + Sodium Acryldimethyl Taurate Copolymer + Squalane + Polysorbate 60 + Sorbitan Isostearate | 1.80 | 18.00 | 1.35 |
| C | Polyacrylate 13 + Polyisobutene + Polysorbate 20 | 3.20 | 32.00 | 2.40 |
| D | Germaben II | 1.00 | 10.00 | 0.75 |
| | | 100.00 | 1000.00 | 75.00 |

*"WS" refers to the internal water-in-silicone inner phase.
**"Gel Phase refers to the aqueous gel outer phase The water-in-silicone emulsion in Table 6 was prepared as follows: Added Phase A compounds in order into a vessel and mixed with a 3 blade propeller at 425 rpm. On addition of the silica the phase thickened temporarily. Used a sweep or Z bar to disperse the silica throughout the phase until the batch resembled a uniform liquid. Added remainder of Phase A and mixed with propeller until uniform. Adjusted the speed of the mixer as needed to avoid splashing, but good movement of the batch. Added Phase B dry mix (powders or pigments) and allowed the batch to "wet" the solids until dispersed evenly through out the batch. Adjusted the speed of the mixer to accommodate the additional solids. Added Phase C, mixed with propeller and homogenized for at least 5 minutes at 2000 rpm. Confirmed batch contained no agglomerations or undispersed powder. Discontinued homogenizer and switched back to propeller mixing. Added Phase D to the main vessel. Mixed until uniform again. In a separate vessel, weighed out Phase E ingredients. In a separate vessel added in specific order (pentylene glycol, glycerin, then preservative). When adding each material mixed until transparent. The liquid initially appeared opaque, but after mixing the solution became clear. Added this to the Phase E material and mixed until transparent. Meter dosed (using a metering pump or dosing equipment, such as a separatory funnel) the water phase to the silicone phase at a rate such that the water phase is added in 30 minutes with moderate to high speed mixing (500-700 rpm—Caframo). Continued mixing at this speed for the time taken to add the water phase. Switched to a homogenizer and mixed at 1 kg of bulk/minute (i.e., a 10 kg batch will mix for 10 minutes at 2000 rpm.). Transferred batch to holding vessel. The water-in-silicone emulsion had a viscosity of 30,000 cps on a Brookfield Viscometer Model RVT with Gyroscope using a T spindle C at 2.5 rpm at 25° C.

The gel phase in Table 6 was prepared as follows: Added each ingredient to a vessel under high shear mixing by using a rotation speed of 1000-3000 rpm with a Greerco Lab scale homogenizer based on 1 kg of bulk per minute creating a high turnover of batch volume. The batch thickened as each of the emulsifiers were added. Homogenized the batch an additional 2-4 minutes to yield a uniform cream gel like appearance. The aqueous-gel outer phase had a viscosity of approximately 100,000 to 140,000 cps on a Brookfield Viscometer Model RVT with Gyroscope using a T spindle C at 2.5 rpm at 25° C.

The three-phase emulsion in Table 6 was prepared in the manner described in Example 3.

Stability of the three-phase emulsion in Table 6 was determined by visual observation which included evaluating the color, odor, appearance, signs of phase separation, texture, application changes, exposure to vigorous mixing (shake test), high temperature exposure (60° C. for 5 days), and Freeze/thaw stability for 5 cycles. The samples were evaluated at 4 week intervals for 12 weeks using samples at 25, 38 and 45° C. The formula was visually stable.

All of the emulsions, compositions containing the emulsions, and methods disclosed and claimed in this specification can be made and executed without undue experimentation in light of the present disclosure. While the emulsions and methods of this invention have been described in terms of certain embodiments, it will be apparent to those of skill in the art that variations may be applied to the emulsions and methods and in the steps or in the sequence of steps of the method described herein without departing from the concept, spirit and scope of the invention. All such variations are deemed to be within the spirit, scope and concept of the invention.

REFERENCES

The following references, to the extent that they provide exemplary procedural or other details supplementary to those set forth herein, are specifically incorporated herein by reference.

U.S. Pat. No. 2,798,053
U.S. Pat. No. 3,755,560
U.S. Pat. No. 4,421,769
U.S. Pat. No. 4,509,949
U.S. Pat. No. 5,011,681
U.S. Pat. No. 5,087,445
U.S. Pat. No. 5,831,080
U.S. Pat. No. 6,235,298
U.S. Pat. No. 6,290,943
U.S. Pat. No. 6,358,500
U.S. Pat. No. 6,464,966
A Guide to Formulating Water-in Silicone Emulsions with Dow Corning 3225C Formulation Aid, Dow Corning, 1995
Barel et al., Handbook of Cosmetic Science and Technology, 511-518, 2001.
European Patent 612,759
International Cosmetic Ingredient Dictionary, 11th Ed., 2006
McCutcheon's, Detergents and Emulsifiers, North American Edition, 1986.
Mitxhell and Schlossman, The Chemistry and Manufacture of Cosmetics: Volume II—Formulating, 7:135-150, 2000.
Mollet et al., In: Formulation Technology: Emulsions, Suspension, Solid Form, 2001.
Sjoblom, In: Emulsions and Emulsion Stability, 2nd Ed., 2005.

The invention claimed is:

1. A water-in-silicone emulsion comprising a discontinuous water phase, a continuous silicone phase, and a silicone polyglucoside emulsifier, wherein the discontinuous water phase does not include a salt.

2. The water-in-silicone emulsion of claim 1, wherein the silicone polyglucoside emulsifier includes an octyl radical and a sugar glucoside.

3. The water-in-silicone emulsion of claim 2, wherein the sugar glucoside is a 6 carbon monosaccharide ranging from 1-8 monomers in length.

4. The water-in-silicone emulsion of claim 3, wherein the silicone polyglucoside emulsifier has a molecular weight of at least 450 daltons.

5. The water-in-silicone emulsion of claim 1, further comprising a co-emulsifier.

6. The water-in-silicone emulsion of claim 5, wherein the co-emulsifier is a glucolipid.

7. The water-in-silicone emulsion of claim 6, wherein the glucolipid includes an alkyl chain 8-20 carbons in length and a glucose portion comprising a 5 carbon monosaccharide.

8. The water-in-silicone emulsion of claim 7, wherein the weight ratio of the silicone polyglucoside emulsifier to the glucolipid co-emulsifier is between 8:1 to 12:1.

9. The water-in-silicone emulsion of claim 1, wherein the silicone polyglucoside emulsifier is present in an amount of between 3% to 8% by weight based on the total weight of the emulsion.

10. The water-in-silicone emulsion of claim 1, comprising a viscosity of 20,000 to 30,000 cps at 25° C. as measured on a Brookfield Viscometer using a TC spindle at 2.5 rpm.

11. The water-in-silicone emulsion of claim 1, wherein the continuous silicone phase comprises a cyclomethicone, an aryl silicone, a dimethicone copolyol, a cyclopentasiloxane, a dimethicone, a short chain siloxanes, or a silicone acrylate, or any combination thereof.

12. The water-in-silicone emulsion of claim 1, wherein the emulsion is comprised in a topical skin composition.

13. The water-in-silicone emulsion of claim 1, wherein the emulsion is comprised in a dermatologically acceptable vehicle.

14. A method of delivering a cosmetic or pharmaceutical active ingredient to skin comprising topically applying a composition comprising a cosmetic or pharmaceutical active ingredient and the water-in-silicone emulsion of claim 1 to skin, wherein topical application of the composition delivers the cosmetic or pharmaceutical active ingredient to the skin.

15. The method of claim 14, wherein the water-in-silicone emulsion comprises a viscosity of 20,000 to 30,000 cps at 25° C. as measured on a Brookfield Viscometer using a TC spindle at 2.5 rpm.

16. The method of claim 14, wherein the silicone polyglucoside emulsifier is present in an amount of between 3% to 8% by weight based on the total weight of water-in-silicone emulsion.

17. The method of claim 14, wherein the silicone polyglucoside emulsifier includes an octyl radical and a sugar glucoside.

18. The method of claim 14, wherein the continuous silicone phase of the water-in-silicone emulsion comprises a cyclomethicone, an aryl silicone, a dimethicone copolyol, a cyclopentasiloxane, a dimethicone, a short chain siloxanes, or a silicone acrylate, or any combination thereof.

19. The method of claim 14, wherein the water-in-silicone emulsion further comprises a co-emulsifier.

20. The method of claim 19, wherein the co-emulsifier is a glucolipid.

\* \* \* \* \*